US005567859A

United States Patent [19]

Emanuele et al.

[11] Patent Number: 5,567,859
[45] Date of Patent: *Oct. 22, 1996

[54] POLYOXYPROPYLENE/POLYOXYETHYLENE COPOLYMERS WITH IMPROVED BIOLOGICAL ACTIVITY

[75] Inventors: R. Martin Emanuele, Alpharetta; Mannarsamy Balasubramanian, Roswell; Hameedsulthan S. Allaudeen, Alpharetta, all of Ga.

[73] Assignee: CytRx Corporation, Norcross, Ga.

[ * ] Notice: The term of this patent shall not extend beyond the expiration date of Pat. No. 5,523,492.

[21] Appl. No.: 292,803

[22] Filed: Aug. 9, 1994

Related U.S. Application Data

[63] Continuation-in-part of Ser. No. 87,136, Jul. 2, 1993, Pat. No. 5,523,492, which is a continuation of Ser. No. 847,874, Mar. 13, 1992, abandoned, which is a continuation-in-part of Ser. No. 673,289, Mar. 19, 1991, abandoned.

[51] Int. Cl.$^6$ ..................................................... C07C 43/11
[52] U.S. Cl. ............................................................ 568/624
[58] Field of Search ............................................... 568/624

[56] References Cited

U.S. PATENT DOCUMENTS 4,764,567  8/1988  Ott .

OTHER PUBLICATIONS

Database WPI, Derwent Publications Ltd., London, GB; AN 82–14781E(08) & JP–A–57 008 223 (mitsui Petrochem.) 16 Jan. 1982. *abstract only*.
Schick, M. J., *Non–ionic Surfactants*, Marcel Dekker Inc., New York, pp. 893–920 (1967).
Schmolka, I., "A Review of Block Polymer Surfactants," *Journal of the American Oil Chemists Society*, 54, No. 3, pp. 110–116 (1977).
Block and Graft Copolymerization, vol. 2, (ed. by R. J. Ceresa, John Wiley & Sons, 1976) "The Applications of Block Copolymer Polyol Surfactants," L. G. Lundsted and I. R. Schmolka; pp. 174–205 and pp. 255–272 (references).
Reindorf, C. A., et al., "Perfluorocarbon Compounds: Effects on the Rheological Properties of Sickle Erythrocytes in vitro," *American Journal of Hematology*, vol. 19, pp. 229–236 (1985).
Padilla, F., et al., "Effect of Fluorocarbon emulsions on the mechanical fragility of normal and sickle cells: in vitro studies," *Federation Proceedings*, vol. 34, pp. 1510–1512 (1975).
Vercellotte, G. M., et al., "Activation of Plasma Complement by Perfluorocarbon Artificial Blood: Probable Mechanism of Adverse Pulmonary Reactions in Treated Patients and Rationale for Corticosteroid Prophylaxis," *Blood*, vol. 59, pp. 1299–1304 (1982).
Rodeheaver, G. T., "Pluronic® F–68: A Promising New Skin Wound Cleanser," *Ann Emerg, Med.*, 9:11, pp. 572–576 (1980).

Janoff, A. S., et al., "The Modification of Human Erythrocyte Membrane Structure by Membrane Stabilizers: An Electron Spin Resonance Study," *American Journal of Hematology*, vol. 10, pp. 171–179 (1981).
Moore, A. R., et al., "Reduction of Splenic Vascular Resistance During Profusion By Pluronic® F–68," *Journal of Surgical Research*, vol. 8, pp. 563–566 (1968).
Benner, K. U., et al., "Cold–Induced Platelet Aggregation In Vivo And Its Inhibition By A Nonionic Surface Active Substance," *Thrombosis Research*, vol. 2, pp. 331–342 (1973).
Hymes, A. C., et al., "The Influence Of An Industrial Surfactant Pluronic® F–68, In The Treatment of Hemorrhagic Shock," *Journal of Surgical Research*, vol. 11, pp. 191–197 (1971).
Hoie, J., et al., "Effects of Pluronic® F68, Poloralkol, On Vascular Resistance In Vivo," *Journal of Surgical Research*, vol. 11, pp. 515–517 (1971).
Grover, F. L. et al., "A Nonionic Surfactant And Blood Viscosity," *Arch. Surg.*, vol. 106, pp. 307–310 (1973).
Grover, F. L. et al., "The Effect of Pluronic® F–68 On Circulatory Dynamics And Renal And Carotid Artery Flow During Hemorrhagic Shock," *Journal of Surgical Research*, vol. 17, pp. 30–35 (1974).
Ketchum, L. D. et al., "Experimental Use of Pluronic® F–68 In Microvascular Surgery," *Plastic and Reconstructive Surgery*, vol. 53, pp. 288–292 (1974).
Ketchum, L. D., "Pharmacological alternations in the clotting mechanism: Use in microvascular surgery," *Journal of Hand Surgery*, vol. 3, pp. 407–415 (1978).
Vasco, K. A., et al., "Poloxalkol® (Pluronic F–68): A priming solution for cardiopulmonary bypass," *Trans. Am. Soc. Artif. Int. Organs*, 18, 526–531 (1972).
Block, N. L., et al., "Acutely Traumatized canine ureter, Effects of low molecular weight dextran and surfactant Pluronic F–68," *Urology*, vol. III 190–194 (1974).
Knize, D. M., et al., "Use of antisludging agents in experimental cold injuries," *Surgery, Gynecology & Obstetrics*, vol. 129, pp. 1019–1026 (1969).

(List continued on next page.)

Primary Examiner—Johann Richter
Assistant Examiner—John Peabody
Attorney, Agent, or Firm—Jones & Askew

[57] ABSTRACT

The present invention comprises novel preparations of polyoxypropylene/polyoxyethylene copolymers which retain the therapeutic activity of the commercial preparations, but substantially reduce the undesirable effects which are inherent in the prior art preparations. Because the preparations of polyoxypropylene/polyoxyethylene copolymers which comprise the present invention are a less polydisperse population of molecules than the prior art polyoxypropylene/polyoxyethylene copolymers, the biological activity of the copolymers is better defined and more predictable and the cardiotoxicity inherent in the native copolymers is substantially reduced.

12 Claims, 14 Drawing Sheets

OTHER PUBLICATIONS

Paton, B. C., et al., *Organ Perfusion and Preservation,* (ed. by Norman, J. C., Appleton–Centry–Crofts (1968), "The use of a nonironic detergent added to organ perfusates," pp. 105–120.

Smillie, J. A., et al., "Cryopreservation of Human Platelets with Polyvinylpyrrolidone," *Transfusion,* vol. 21, pp. 552–556 (1981).

Gaehtgens, P., et al., "Disaggregation of Human Red Blood Cells by Various Surface–Active Agents as Related to Changes of Cell Shape and Hemolysis," *Act Heamat.,* vol. 33 pp. 82–89 (1975).

Sugi, et al., "The use of Fluosol–DA (FDA) in emergency situations: a report of 67 clinical cases," Abstract/451. *Advances in Blood Substitute Research* ed. by Bolin, et al., Alan R. Liss, Inc. New York (1983).

Lane, T. A., et al., "Reduction in the toxicity of a component of an artificial blood substitute by supercritical fluid fractionation," *Transfusion,* vol. 28, pp. 375–378 (1987).

Lane, T. A., et al., "Paralysis of Phagocyte migration due to an artificial blood substitute," *Blood,* vol. 64, pp. 400–405 (1984).

Spiess, B. D., et al., "Protection from cerebral air emboli with perfluorocarbons in rabbits," *Stroke,* vol. 17, pp.b 1146–1149 (1986).

Kanter, K. R., et al., "Superiority of perfluorocarbon cardioplegia over blood or crystalloid cardioplegia," *Circulation,* vol. 64. II75–II80 (1981).

Harjula, A., et al., "Perfluorocarbon solution as a myocardial preservative," *J. Applied Cardiology,* vol. 2, pp. 121–136 (1987).

Tokioka, M. D., et al., "Effects of introcoronary infusion of arterial blood or Fluosol–DA 20% on regional myocardial metabolism and function during brief coronary artery occlusions," *Laboratory Investigation,* vol. 75, pp. 473–481 (1987).

Forman, M. B., et al., "Reduction of infarct size within intracoronary perfluorochemical in a canine preparation of reperfusion," *Circulation,* vol. 71, pp. 1060–1068 (1985).

Forman, M. B., et al., "Beneficial long–term effect on intracoronary perfluorochemical on infarct size and ventricular function in a canine reperfusion model," *J. Am. Col. of Cariol,* pp. 1082–1090 (May 1987).

Goodman, R. L., et al., "Perfluorocarbon emulsions in cancer therapy: preliminary observations on presently available formulations," *Int. J. Radiation Oncology Viol. Phys.,* vol. 10, pp. 1421–1424 (1984).

Perfluorochemical Blood Substitutes, Technical Information Ser. No. 5, Jun. 30, 1978, Revised, Jul. 1, 1981, Manufacturer: The Green Cross Corporation.

Connaghan et al., "Specific Identifications of Fibrin Polymers, Fibrinogen Degradation Products, and Cross linked Fibrin Degration Products in Plasma and serum with a New Sensitvie Technique," *Blood,* vol. 65, No. 3, pp. 589–597 (Mar. 1985).

Atkinson et al., "Iontransport mediated by copolymers composed of polyoxyethylene and polyoxypropylene," *The American Physiological Society,* 0363–6143/88, pp. C20–C26 (1988).

Wiman et al., "Determination of Soluble Fibrin in Plasma by a Rapid and Quantitative Spectrophotometric Assay," Thrombosis and Haemostasis, F. K. Schattauer Verlag GmbH (Stuttgart) 55(2), pp. 18–193 (1986).

Hunter et al., "The Adjuvant Activity of nonionic Block Polymer Surfactanst," Scand. J. immunol., No. 23, pp. 287–300 (1986).

Hunter et al., "The Adjuvant Activity of Nonionic Block Polymer Surfactants. I. The Role of Hydrophile–Lipophile Balence," *J. Immunol.,* vol. 127, No. 3, pp. 1244–1250 (1981).

Hunter et al., "Nonionic block copolymer surfactants as immunological adjuvants: Mechanisms of action and novel formulation," *Immunological Adjuvants and Vaccines, ed. Gregoriadis et al., Plenum Publishing Corp., pp. 133–144 (1989).*

Byars et al., "Adjuvant Formulation for Use in Vaccines to Elicit cell–Mediated and Humoral Immunity," *Vaccine,* vol. 5, pp. 223–228 (Sep. 1987).

POLYOXYPROPYLENE/POLYOXYETHYLENE COPOLYMERS WITH IMPROVED BIOLOGICAL ACTIVITY

CROSS-REFERENCE TO RELATED APPLICATIONS

This patent application is a continuation-in-part of U.S. patent application Ser. No. 08/087,136, filed on Jul. 2, 1993, which is a continuation of U.S. patent application Ser. No. 07/847,874, filed on Mar. 13, 1992, now abandoned, which is a continuation-in-part of U.S. patent application Ser. No. 07/673,289, filed Mar. 19, 1991, now abandoned.

TECHNICAL FIELD

The present invention relates to a preparation of polyoxypropylene/polyoxyethylene copolymer which has an improved activity and toxicity profile. The present invention also includes purified polyoxypropylene/polyoxyethylene block copolymers with substantially no unsaturation, substantially free of low molecular weight molecules and a narrowed polydispersity value.

BACKGROUND OF THE INVENTION

Certain polyoxypropylene/polyoxyethylene copolymers have been found to have beneficial biological effects when administered to a human or animal. A group of polyoxypropylene/polyoxyethylene copolymers have been found to inhibit the growth of microorgansims, such as bacteria, yeasts and viruses. For example, these surface-active copolymers have been shown to inhibit human immunodeficiency virus (HIV), Mycobacteria species and *Toxoplasma gondii*.

The antiinfective activity of the surface active copolymers and the use of the surface active copolymers as therapeutic delivery agents are described in detail in copending U.S. patent applications Ser. Nos. 08/161,551 and 08/138,271 both of which are incorporated herein by reference.

The surface-active copolymers are effective in treating a viral infection in a human or animal including infections caused by the HIV or related viruses. The present invention provides a composition that can be administered to patients who are infected with HIV or similar viruses. The surface-active copolymer is effective in inhibiting or suppressing the replication of the HIV and related virus strains in cells.

The surface-active copolymers are useful for treating infections caused by microorganisms when used alone or with a conventional antibiotic. Several conventional antibiotics that can be used with the surface-active copolymer include, but are not limited to, rifampin, isoniazid, ethambutol, gentamicin, clindamycin, pyrimethamine, tetracycline, and erythromycin.

The surface active copolymers can be used to deliver therapeutic drugs to a human or animal for treating disease states such as, but not limited to, bacterial infection and infections caused by HIV and other DNA and RNA viruses. The methods relate particularly to compositions and methods for treating infectious diseases and genetic disorders through gene therapy and intracellular delivery of antisense oligonucleotides or other nucleic acid sequences.

The surface active copolymers are effective for treating a disease state comprising an administerable admixture of an effective amount of a therapeutic compound capable of altering nucleic acid sequence function and an effective amount of the surface active nonionic block copolymer.

The surface active copolymers can be used in an admixture of a compound capable of altering gene expression and/or protein translation, such as an antisense oligonucleotide, a triplex DNA compound, a ribozyme or other compound capable of altering nucleic acid sequence function, and the surface active copolymer.

Because the commercially available sources of the polyoxypropylene/polyoxyethylene copolymers have been reported to contain components that exhibit toxicity as well as variation in biological activity, what is needed is a preparation of polyoxypropylene/polyoxyethylene copolymers which retain the therapeutic activities of the commercial preparations but are free from their other biological activities such as toxicity. It is well known in the art that the unsaturation is produced during the polymerization of the polypropylene hydrophobe and unsaturation results in reduced functonality and reduced stability. The reduced functionality results in the formation of impurities with diblock type structure upon subsequent polymerization of the hydrophobe with ethylene oxide. Therefore what is needed is a composition with less unsaturation and less diblock type impurities. In addition, what is needed is a preparation of polyoxypropylene/polyoxyethylene copolymers which is less polydisperse in molecular weight, more stable, is less cardiotoxic, and is more efficacious.

SUMMARY OF THE INVENTION

The present invention comprises novel preparations of polyoxypropylene/polyoxyethylene copolymers which are effective as antiinfective agents, but are free from the undesirable effects, such as cardiotoxicity, which are inherent in the prior art preparations. The polyoxypropylene/polyoxyethylene copolymers which comprise the present invention (1) are a less polydisperse population of molecules which results in better and more predictable pharmacologic activity, (2) is comprised of a population of molecules that are less cardiotoxic compared to the copolymers of the prior art, (3) are substantially free of unsaturated molecules and low molecular weight by products. The polyoxypropylene/polyoxyethylene copolymers have greater product stability and shelf life than the poyoxyethylene/polyoxypropylene copolymers of the prior art.

The antiinfective composition of the present invention comprises a surface active copolymer. The surface active copolymer can be an ethylene oxide-propylene oxide condensation product with the following general formula:

$$HO(C_2H_4O)_b(C_3H_6O)_a(C_2H_4O)_bH$$

wherein "a" is an integer such that the polypropyleneoxide hydrophobe represented by $(C_3H_6O)$ has a molecular weight of approximately 1,200 to approximately 15,000, preferably between approximately 1,500 and approximately 5300, more preferably between approximately 1750 Daltons and approximately 4500 Daltons, still more preferably between approximately 2250 Daltons to approximately 4000 Daltons, and "b" is an integer such that the polyethyleneoxide hydrophile portion represented by $(C_2H_4O)$ constitutes approximately 1% to approximately 50% by weight of the copolymer compound, preferably approximately 5% to approximately 45% by weight of the copolymer compound, more preferably approximately 10% to approximately 30%, and still more preferably approximately 15% to approximately 20%. The copolymer of the present invention has a polydispersity value of less than approximately 1.17.

The present invention includes polyoxypropylene/polyoxyethylene block copolymers with polydispersity values of less than 1.17. Commercially available poloxamers, for example poloxamer 331, has a polydispersity value as high as approximately 1.41. The purification of the polyoxypropylene polymer can be performed by gel permeation chromatography or other procedures that are well known to those of ordinary skill in the art. The present invention also includes a novel separation process of supercritical fluid extraction using carbon dioxide to purify polyoxypropylene/polyoxyethylene block copolymers to reduce the polydispersity values less than 1.17. In addition, the present invention incudes poyoxyethylene/polyoxypropylene copolymers with polydispersity values less than 1.17 that have been synthesized by a process described in patent application Ser. No. 08/292,814, now U.S. Pat. No. 5,523,492.

Accordingly, it is an object of the present invention to provide a surface-active copolymer with antiinfective activities with substantially no unsaturation, with fewer toxic side effects and with substantially no low molecular weight impurities, including diblock type impurities It is another object of the present invention to provide a more homogeneous polyoxypropylene/polyoxyethylene copolymer relative to the molecular weight range.

It is another object of the present invention to provide a preparation of polyoxyethylene/polyoxypropylene block copolymer with a polydispersity value of less than 1.17.

It is another object of the present invention to provide a preparation of polyoxyethylene/polyoxypropylene block copolymer with substantially no unsaturation and reaction by-products.

It is yet another object of the present invention to provide a surface-active copolymer which has less cardiotoxicity and less detergent-like activity.

It is yet another object of the present invention to provide a surface-active copolymer that can be used safely in both humans and animals as an antimicrobial agent.

It is yet another object of the present invention to provide a surface-active copolymer that has a better therapeutic index than commercially available surface-active copolymers in both humans and animals when used as an antibacterial, an antiviral, an antifungal and an antiprotozoal agent.

These and other objects, features and advantages of the present invention will become apparent after a review of the following detailed description of the disclosed embodiments and the appended claims.

DETAILED DESCRIPTION

Figure 1A:
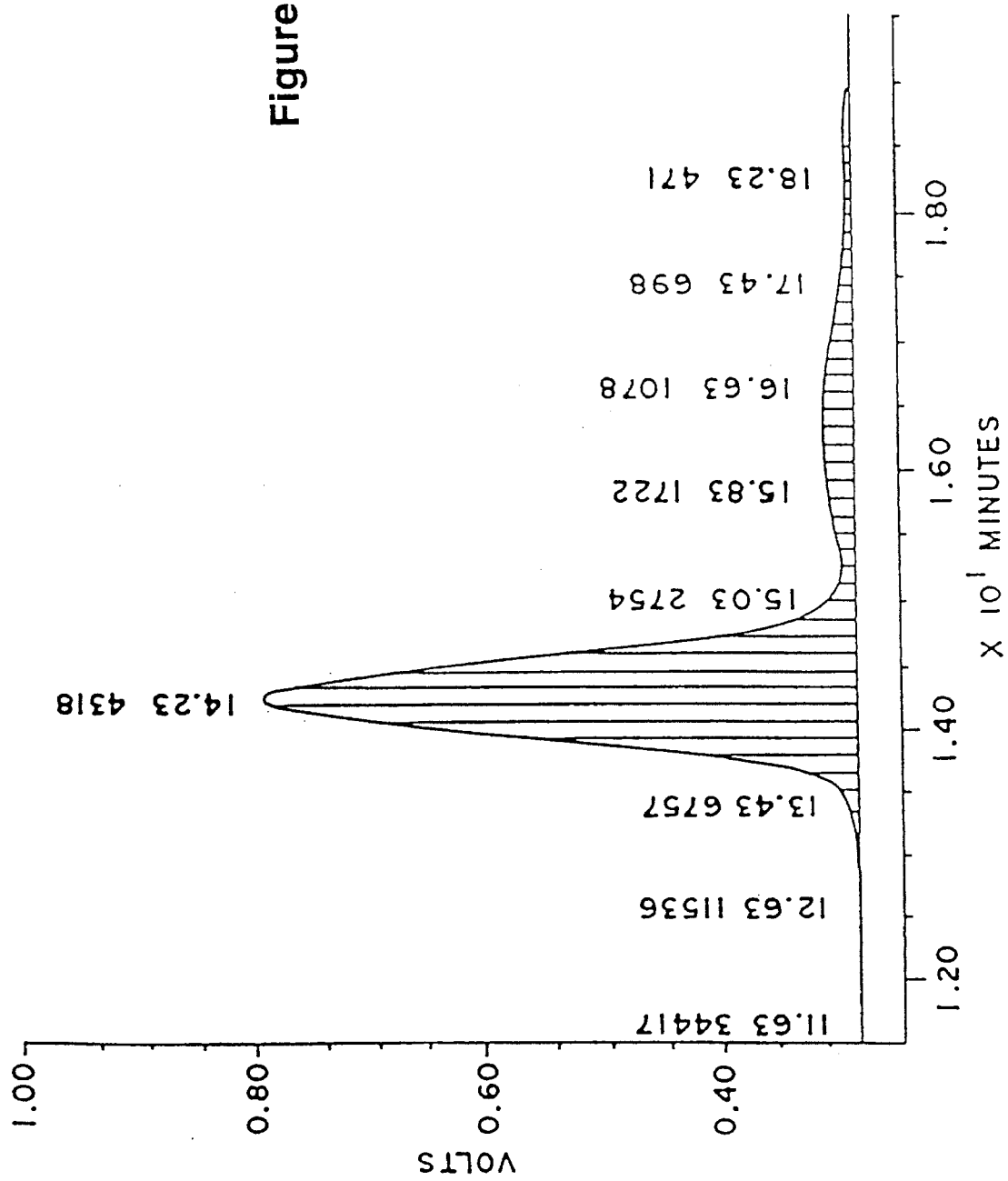
FIGS. 1A through 1C are gel permeation chromatograms of native and GPC fractions of fractionated poloxamer 331.

Although the prior art preparations of polyoxypropylene/polyoxyethylene block copolymers may have been suitable for industrial uses, it has been determined that the newly discovered uses for the copolymers as therapeutic agents require less polydisperse populations of molecules in the preparations. It is important that the molecules that are to be used to treat humans or animals have less toxicity and less unsaturation than the prior art preparations of the polyoxypropylene/polyoxyethylene block copolymers.

The present invention comprises polyoxypropylene/polyoxyethylene copolymers that have a polydispersity value of less than 1.17. The novel copolymers can be prepared by removing disparate molecules from the prior art preparation or by synthesizing the copolymer according to the method disclosed in copending patent application Ser. No. 08/292, 814 now U.S. Pat. No. 5,523,492 which is incorporated herein by reference. The method of preparation of the copolymers of the present invention also includes the purification of the polyoxypropylene block of the polyoxypropylene/polyoxyethylene copolymer before the polyoxyethylene blocks are added to the molecule. In this way, the partially polymerized polyoxypropylene polymers, including those containing monofunctional unsaturated polymers, are removed before the addition of polyoxyethylene polymers to the molecule. This results in a polyoxypropylene/polyoxyethylene block copolymer that is within the physical parameters which are contemplated as the present invention.

The antiinfective composition of the present invention comprises a surface active copolymer. The surface active copolymer can be an ethylene oxide-propylene oxide condensation product with the following general formula:

$$HO(C_2H_4O)_b(C_3H_6O)_a(C_2H_4O)_bH$$

wherein "a" is an integer such that the polypropyleneoxide hydrophobe represented by $(C_3H_6O)$ has a molecular weight of approximately 1,200 to approximately 15,000, preferably between approximately 1,500 and approximately 5300, more preferably between approximately 1750 Daltons and approximately 4500 Daltons, still more preferably between approximately 2250 Daltons to approximately 4000 Daltons, and "b" is an integer such that the polyethyleneoxide hydrophile portion represented by $(C_2H_4O)$ constitutes approximately 1% to approximately 50% by weight of the copolymer compound, preferably approximately 5% to approximately 45% by weight of the copolymer compound, more preferably approximately 10% to approximately 30%, and still more preferably approximately 15% to approximately 20%. The copolymer of the present invention has a polydispersity value of less than approximately 1.17.

The present invention includes polyoxypropylene/polyoxyethylene block copolymers with polydispersity values of less than 1.17. Commercially available poloxamer 331 (PLURONIC®L101, BASF, Parsipanny, N.J.) has a typical polydispersity value as high as approximately 1.41. The purification of the polyoxypropylene polymer can be performed by gel permeation chromatography, or other procedures that are well known to those of ordinary skill in the art. It can also be purified by supercritical fluid extraction process. Alternatively, these polymers with significantly reduced polydispersity values can be synthesized using novel synthetic processes. These synthetic processes are described in copending U.S. patent application Ser. No. 08/292,814, now U.S. Pat. No. 5,523,492.

A preferred ethylene oxide-propylene oxide copolymer for use in the antiinfective composition of the present invention is a copolymer having the following formula:

$$HO(C_2H_4O)_b(C_3H_6O)_a(C_2H_4O)_bH$$

wherein "a" is an integer such that the polypropyleneoxide hydrophobe represented by $(C_3H_6O)$ has a molecular weight of about 1,750 to 4,500 Daltons and "b" is an integer such that the polyethyleneoxide hydrophile portion represented by $(C_2H_4O)$ constitutes approximately 10% to 40% by weight of the copolymer compound.

Another especially preferred embodiment of the antiinfective compound of the present invention is the compound with the following general formula:

$$HO(C_2H_4O)_b(C_3H_6O)_a(C_2H_4O)_bH$$

wherein the mean aggregate molecular weight of the hydrophobic portion of the triblock copolymer, consisting of polyoxypropylene (POP) is approximately 2500 to 3500 Daltons; the hydrophile portion represented by polyoxyethylene (POE) constitutes approximately 10% to 40% of the total weight of the copolymer compound.

Another especially preferred embodiment of the antiinfective compound of the present invention is the compound with the following general formula:

$$HO(C_2H_4O)_b(C_3H_6O)_a(C_2H_4O)_bH$$

wherein the mean aggregate molecular weight of the hydrophobic portion of the triblock copolymer, consisting of polyoxypropylene (POP) is approximately 3100 Daltons; the hydrophile portion represented by polyoxyethylene (POE) constitutes approximately 15% of the total weight of the copolymer compound.

Ethylene oxide-propylene oxide condensation products which may be employed in the present invention are summarized in Table I. The polypropyleneoxide hydrophobe (polyoxypropylene) molecular weights are given as approximate midpoints of molecular weight ranges. It is to be understood that these compounds are merely representative of the compounds that can be used to practice the present invention and do not include all possible compounds that could be used to practice the present invention. The high molecular weight copolymers listed in Table I that do not have a BASF tradename are novel compositions that have never been synthesized before. These novel compounds are available from CytRx Corporation, Norcross, Ga. Actual weight percentage may not match with the values reported by the manufacturer

TABLE I

| CRL # | Poloxamer | BASF Trade Name | Molecular Weight of POP | % POE |
|---|---|---|---|---|
|  | 122 | L42 | ≈1200 | ≈20% |
| CRL85171 | 181 | L61 | ≈1750 | ≈10% |
| CRL85172 | 182 | L62 | ≈1750 | ≈20% |
| CRL85173 | 183 | L63 | ≈1750 | ≈30% |
| CRL85174 | 184 | L64 | ≈1750 | ≈40% |
| CRL85175 | 185 | P65 | ≈1750 | ≈50% |
| CRL85178 | 188 | F68 | ≈1750 | ≈80% |
| CRL85202 | 212 | L72 | ≈2050 | ≈20% |
| CRL85221 | 231 | L81 | ≈2250 | ≈10% |
| CRL8122 | 282 | L92 | ≈2750 | ≈20% |
| CRL8131 | 331 | L101 | ≈3250 | ≈10% |
| CRL8133 | 333 | P103 | ≈3250 | ≈30% |
| CRL8135 | 335 | P105 | ≈3250 | ≈50% |
| CRL9038 | 338 | F108 | ≈3250 | ≈80% |
| CRL8141 | 401 | L121 | ≈4000 | ≈10% |
| CRL8142 | 402 | L122 | ≈4000 | ≈20% |
| CRL8143 | 403 | P123 | ≈4000 | ≈30% |
| CRL8941 | 441 | L141 | ≈4400 | ≈10% |
| CRL8950 | — | — | ≈9000 | ≈5% |
| CRL1235 | — | — | ≈7500 | ≈5% |
| CRL1190 | — | — | ≈10,000 | ≈5% |
| CRL1183 | — | — | ≈3750 | ≈10% |
| CRL1122 | — | — | ≈5900 | ≈12% |
| CRL3362 | — | — | ≈3900 | ≈11% |
| CRL3632 | — | — | ≈4740 | ≈11% |
| CRL9352 | — | — | ≈7750 | ≈15% |
| CRL-1018 | — | — | ≈3100 | ≈15% |
| CRL1187 | — | — | ≈750 | ≈25% |

Although molecular weight averages are important and useful when characterizing polymers in general, it is important to know the molecular weight distribution of a polymer. Some processing and end-use characteristics (melt flow, flex life, tensile strength, etc.) are often predicted or understood by observing the values and/or changes occurring in specific molecular weight averages and polydispersity values. A list of the processing characteristics follows.

| Molecular Weight Averages | Processing Characteristics |
|---|---|
| Mz | Flex life/stiffness |
| Mn | Brittleness, flow |
| Mw | Tensile strength |

These molecular weight values can also be correlated with the biological properties of polyoxypropylene/polyoxyethylene copolymers. The breadth of the distribution is known as the polydispersity (D) and is usually defined as Mw/Mn. A monodisperse sample is defined as one in which all molecules are identical. In such a case, the polydispersity (Mw/Mn) is 1.0. Narrow molecular weight standards have a value of D near 1 and a typical polymer has a range of 2 to 5. Some polymers have a polydispersity in excess of 20.

The equations for expressing various average molecular weights and polydispersity (from GPC chromatography) are as follows:

$$\bar{M}_n = \text{Number Average} = \frac{\Sigma \text{Area}_i}{\Sigma \text{Area}_i/M_i}$$

$$\bar{M}_w = \text{Wt. Average} = \frac{\Sigma[(\text{Area}_i)(M_i)]}{\Sigma(\text{Area}_i)}$$

$$\overline{M}_z = Z \text{ average} = \frac{\Sigma[(\text{Area}_i)(M_i)^2]}{\Sigma[(\text{Area}_i)(M_i)]}$$

$$\overline{M}_{z+1} = Z+1 \text{ average} = \frac{\Sigma[(\text{Area}_i)(M_i)^3]}{\Sigma[(\text{Area}_i)(M_i)^2]}$$

$$\text{Polydispersity}(D) = \frac{\overline{M}_w}{\overline{M}_n}$$

where:

Area$_i$= area of the ith slice

M$_i$= molecular weight of the ith slice

Thus, by calculating the parameters listed above, one can specify a certain polydispersity that is acceptable for a pharmaceutical preparation. A high polydispersity value indicates a wide variation in size for the population of molecules in a given preparation while a lower polydispersity value indicates less variation. Because molecular size is an important determinant of biological activity, it is important to restrict the dispersity of the molecules in the preparation in order to achieve a more predictable and homogeneous biological effect. Thus, the polydispersity measurement can be used to measure the dispersity of molecules in a preparation and correlates to that compound potential for variation in biological activity.

It is to be understood that the polydispersity values that are described herein were determined from GPC chromatograms which were obtained using a Model 600E Powerline chromatographic system equipped with a column heater module, a Model 410 refractive index detector, Maxima 820 software package (all from Waters, Milford, Mass.), two LiChrogel PS-40 columns and a LiChrogel PS-20 column in series (EM Science, Gibbstown, N.J.), or Ultra styragel GPC columns (by Waters, Milford, Mass.) and polyethylene glycol molecular weight standards (Polymer Laboratories, Inc., Amherst, Mass.). Polydispersity values obtained using this system are relative to the chromatographic conditions, the molecular weight standards and the size exclusion characteristics of the gel permeation columns. Polydispersity measurements using different separation principles may give absolute polydispersity values which are different from those described herein. However, one of ordinary skill in the art can easily convert any polydispersity value that is obtained using a different separation method to the values described herein simply by running a single sample on both systems and then comparing the polydispersity values from each chromatogram.

In accordance with the present invention, a composition is provided that is a polyoxypropylene/polyoxyethylene triblock copolymer that has a polydispersity value of less than 1.17. Preferably, the polydispersity value is less than approximately 1.10, with a most preferred polydispersity value of 1.05. It is to be understood that the present invention includes, but is not limited to, poloxamer compounds.

Another method of describing one of the preferred embodiments of the present invention is to describe the copolymer in terms of the percent of the unfractionated or native copolymer that is purified. For example the preferred embodiment is at least a substantially pure block copolymer having the formula

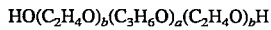

wherein the molecular weight of the polypropyleneoxide hydrophobe ($C_3H_6O$) is approximately 3100 Daltons and the average molecular weight of the compound is approximately 3700 Daltons, and wherein the block copolymer comprises at least 85 percent by weight of high molecular weight fraction, and not more than 15 percent by weight of a low molecular weight impurity when fractionated by gel permeation chromatography or supercritical fractionation.

The surface-active copolymers of the present invention can be prepared in a number of ways. The polydispersity value of the commercially available compounds can be reduced by subjecting commercially available compounds to well known fractionation procedures such as gel permeation chromatography or supercritical fluid extraction. In addition, the compounds can be subjected to molecular sieving techniques that are known to those of ordinary skill in the art.

The surface-active copolymers of the present invention have been shown to be effective with only one administration to the patient. However, in most cases, subsequent administrations will be necessary to achieve maximum efficiency. The mode of administration can be topical, transdermal, transmucosal, oral, inhalation, subcutaneous, intramuscular or intravenous. The preferred mode of injection is intravenous. The optimum amount of the antiinfective compound of the present invention in a dose varies with the weight of the patient being treated. The effective dose range generally includes dosages of 0.1 mg/Kg/day to 50 mg/Kg/day. A preferred dosage range is 0.5 mg/Kg/day to 25 mg/Kg/day. A more preferred dosage range is 1 mg/Kg/day to 10 mg/Kg/day. It has been surprisingly found that effective therapy is provided even when the block copolymer and the therapeutic drug are administered separately, either by the same or different routes of administration, and either simultaneously or at different times.

The surface-active copolymers form micelles above their critical micelle concentration. The non-ionic copolymers have negative thermal coefficients of solubility. In the cold, the kinetic energy of water molecules is reduced and they form weak hydrogen bonds with the oxygen of the POP blocks. This hydration of the hydrophobe promotes solubility at low temperatures. As the temperature rises, the "cloud point" is reached; the increased kinetic energy of the water breaks the hydrogen bonds, the polymer becomes insoluble and micelles form.

Thus, the surface-active copolymers can form physical structures that can be combined or loaded with an additional, distinct therapeutic agent. Consequently, the nonionic block copolymers of the present invention can be used as therapeutic drug delivery vehicles. Admixtures of therapeutic drugs with non-ionic block copolymers have the advantage of synergistic activity of two therapeutic agents. Further, surface-active copolymers having specific characteristics can be selected for use with particular therapeutic drugs. For example, CRL8131, which is hydrophobic, is an excellent carrier for hydrophobic antibiotics such as rifampin. However, other agents which are not distinctly hydrophobic can be used according to the present invention.

A therapeutic delivery composition is prepared using any of the surface-active copolymers of the present invention in combination with any of a variety of antimicrobial agents. In a preferred embodiment CRL8131 is used in a concentration of approximately 3% to approximately 5% to construct a therapeutic delivery vehicle. Therapeutic delivery vehicles made using copolymers that are more hydrophilic than CRL8131 normally require a higher concentration (approximately 5% to approximately 10%) of the copolymer.

Using copolymer-based micelles as a therapeutic drug delivery vehicles is particularly desirable because the micelles are accumulated readily and are present for an extended period of time, in macrophages, the site of HIV and other viral infections and a major target for viral therapy. Examples of such therapeutic copolymer-based therapeutic compositions include, but are not limited to, CRL8131 combined with 2% Tween 80 and 1% ethanol. Other pharmaceutically acceptable vehicles may be used in effectively delivering the surface-active copolymers.

Alternatively, nonionic block copolymers of the present invention and therapeutic drugs may be administered to a human or animal separately, either simultaneously or at different times. For example, copolymers such as CRL8131 or CRL8142 are administered by injection, followed by administration of the therapeutic drug. Administration of the drug may be by any normal route such as, injection, topical or transdermal application, trans-mucosal absorption, inhalation or oral ingestion.

It should be understood that the molecular weight range that is described as the optimum range for the copolymer is to be considered the outside range and that any population of molecules that fall within that range are considered as embodiments of the present invention.

EXAMPLE I

Figure 1B:
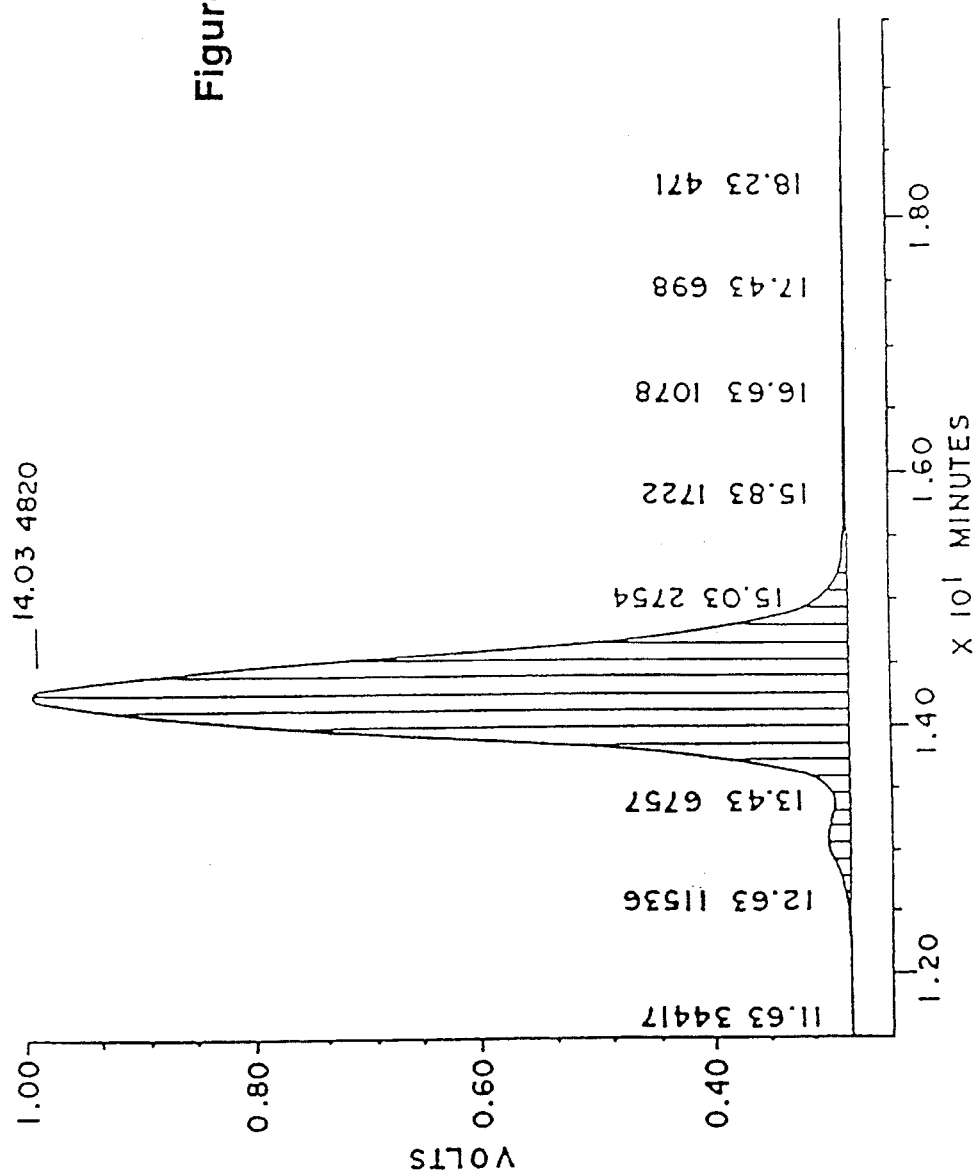
Figure 1C:
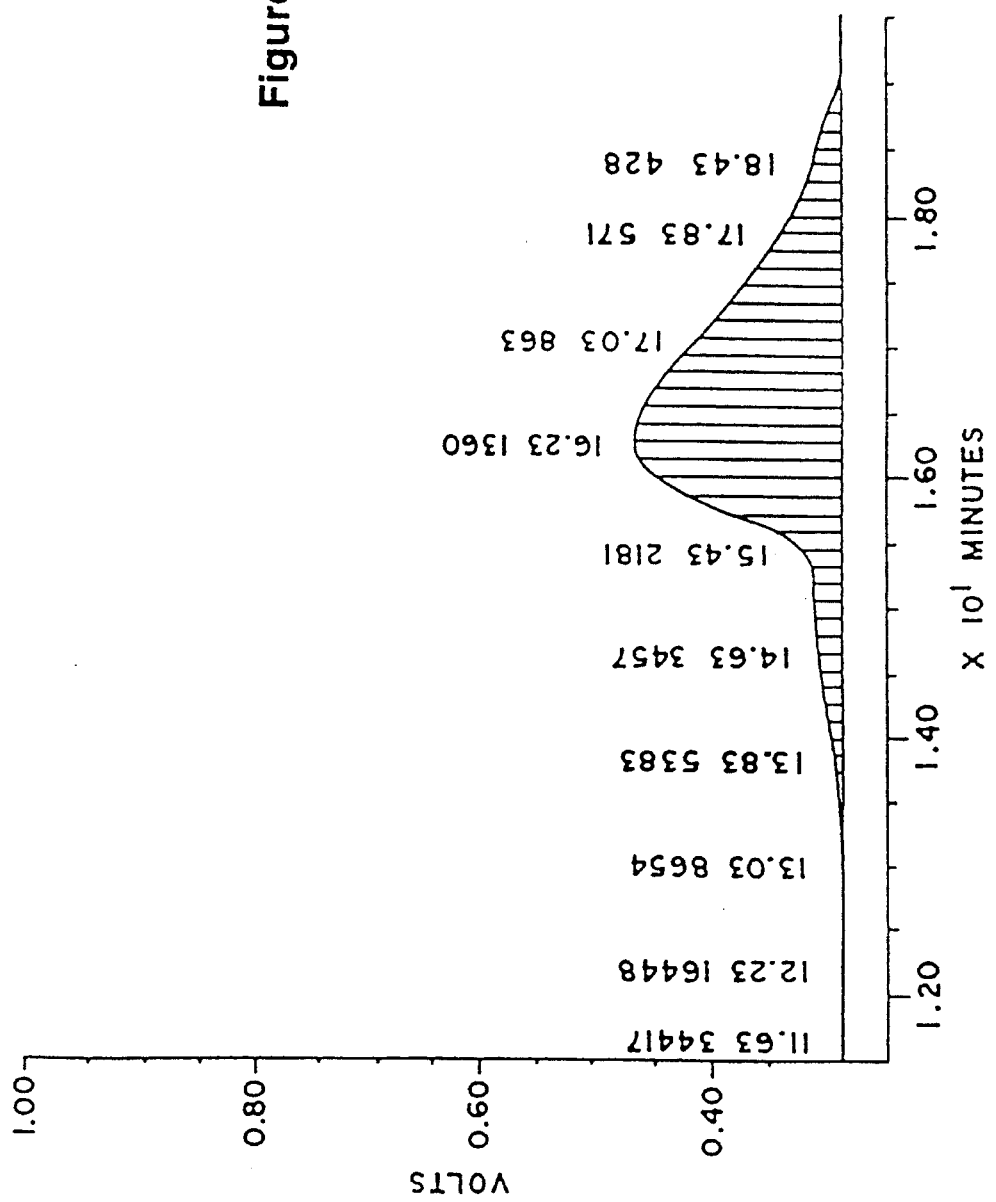

Poloxamer 331 (Pluronic®L101, BASF Corporation, Parsippany, N.J.) was fractionated as follows: Poloxamer 331 (BASF Corporation, Parsippany N.J.) is dissolved in tetrahydrofuran at a concentration of 20 mg/mL. A Model 600E Powerline chromatographic system equipped with a column heater module, a Model 410 refractive index detector and Maxima 820 software package (all from Waters, Div. of Millipore, Milford, Mass.) is used to fractionate the commercially prepared polyoxamer 760.5 copolymer. The chromatographic system is equipped with Ultrastyragel $10^3$ A and 500 A in series (Waters, Div. of Millipore, Milford, Mass.). Column size is 7.8 mm internal diameter by 30 cm. Precolumn filters #A-315 with removable 2 μm frits (Upchurch Scientific, Oak Harbor, Wash.) were used for protection of the columns. 200 μL (4 mg) of the poloxamer 760.5 in tetrahydrofuran is added to the column and the sample is run with the columns at 40° C. and the detector at 45° C. The chromatographs for native poloxamer 331, an early eluting fraction and a late eluting fraction are shown in FIGS. 1A through 1C respectively. All proton NMR analyses were performed in accordance with the NF procedure "Weight Percent Oxyethylene" on a Bruker 300 MHz instrument. The results of these spectra and chromatograms are summarized in Table II.

TABLE II

| Fraction | % POE[a] | MW[b] | Unsaturation[c] |
|---|---|---|---|
| Native | 17 | 4045 | Yes |
| HMW Purified Fraction | 15 | 4452 | No |
| LMW Impurity | 31 | 1466 | Yes |

[a]As measured by NMR
[b]As measured by gel permeation chromatography
[c]As measured by NMR When the poloxamer number for each fraction is calculated based on the empirical data collected, it is seen that the low molecular weight impurities are very different in structure when compared to the native preparation. In addition, the unsaturated population of molecules have been substantially removed by the fractionation procedure.

EXAMPLE II

CRL8131 was fractionated by supercritical fluid extraction. About 2350 grams of CRL8131 was mixed with 1604 grams of Hydromatrix (Varian) and loaded into an extraction vessel. A process development unit (PDU) with $CO_2$ recycling capability was used. Supercritical $CO_2$ was continuously passed through the extraction cell with an upward flow. The extraction cell was maintained at 40° C. Several fractions were collected by varying the pressure of supercritical $CO_2$. The extraction conditions and the amount of each fraction collected are given in Table III along with the characterization results.

The fractions were characterized by Gel Permeation Chromatography using PEG standards, NMR, residual ethylene glycol and propylene glycol and unsaturation. Gel Permeation Chromatography provided different weight average molecular weights. Percentage of ethylene oxide units was determined from NMR. Unsaturation was measured by wetchemistry and provided amount of —CH=CH— groups present in the end groups.

EXAMPLE III

As shown in Table III, fractions 159-21-1 through 159-21-6 were collected with supercritical $CO_2$ pressure at 2200 psi, fractions 159-21-7 through 159-21-11 were collected at 3400 psi, and fractions 159-21-12 through 159-21-17 were collected at 4400 psi. Fraction 159-21-18 is the component that is soluble in liquid $CO_2$. Fraction 159-21-19 is what is left in the extraction after the extraction process (material that was not extractable during the fractionation). Fraction 159-21-20 is the starting material before extraction.

TABLE III

Characterization of CRL8131 Fractions (Obtained by Supercritical Fluid Extraction

| Fractions Lot # | Amount Collected gm | Mn | Mw | Mp | PD | EG/PG ppm | % EO | Unsaturation mEq/gm | Moles of Unsaturation per Mole of Polymer |
|---|---|---|---|---|---|---|---|---|---|
| 159-21-1* | 2.5 | 934 | 1101 | 1051 | 1.18 | None/None | — | 0.7166 | 0.67 |
| 159-21-2* | 12.1 | 806 | 945 | 895 | 1.17 | 36.1/60.2 | 31.7 | 0.752 | 0.61 |
| 159-21-3 | 15.5 | 758 | 882 | 822 | 1.16 | 62.4/82.6 | — | — | — |
| 159-21-4 | 35.9 | 782 | 941 | 858 | 1.2 | — | 32 | — | — |
| 159-21-5 | 21.3 | 826 | 980 | 934 | 1.19 | — | — | 0.7638 | 0.63 |
| 159-21-6 | 17.8 | 879 | 1040 | 1016 | 1.18 | 84.0/83.2 | 33.9 | 0.7746 | 0.68 |
| 159-21-7 | 38.9 | 1059 | 1270 | 1154 | 1.2 | — | — | — | — |
| 159-21-8 | 36 | 1231 | 1507 | 1312 | 1.22 | — | 31.6 | 0.7049 | 0.87 |
| 159-21-9 | 17.5 | 1327 | 1645 | 1369 | 1.24 | — | — | — | — |
| 159-21-10 | 24.4 | 1484 | 1877 | 1429 | 1.26 | — | 29.5 | 0.5026 | 0.75 |
| 159-21-11 | 14.2 | 1611 | 2121 | 1505 | 1.32 | 67.9/59.8 | — | 0.4634 | 0.75 |
| 159-21-12 | 29.5 | 2007 | 2510 | 3487 | 1.25 | — | 22.7 | 0.3273 | 0.66 |
| 159-21-13 | 30.7 | 2349 | 2862 | 3664 | 1.22 | — | — | — | — |
| 159-21-14 | 27.5 | 2625 | 3064 | 3487 | 1.17 | — | — | — | — |
| 159-21-15 | 23.8 | 2825 | 3198 | 3487 | 1.13 | — | — | 0.1271 | 0.36 |
| 159-21-16 | 22.7 | 2970 | 3296 | 3487 | 1.11 | — | — | — | — |
| 159-21-17 | 21.9 | 3110 | 3378 | 3487 | 1.09 | — | 11.1 | — | — |
| 159-21-18* | ** | 1075 | 2734 | 3700 | 2.54 | 2686.2/351.2 | 11.9 | 0.7779 | 0.84 |
| 159-21-19 | *** | 4112 | 4266 | 4091 | 1.04 | (304.6)/None | 14.7 | 0.0013 | 0.0053 |
| 159-21-20 | **** | 3219 | 3988 | 4305 | 1.24 | — | 15.8 | 0.1064 | 0.34 |

Supercritical Fluid Extraction Conditions:
Carbon Dioxide Flow rate = 1400 mL/min. Temperature = 40 C.
Fractions 1 through 6 collected at 2200 psi
Fractions 7 through 11 collected at 3400 psi
Fractions 12 through 17 collected at 4400 psi
*Slightly Yellow
**Evaporated the carbon dioxide solution at the separator (liquid carbon dioxide soluble fraction)
***Left behind at the extractor
****Starting CRL8131, mixed with hydromal

EXAMPLE IV

Figure 2:
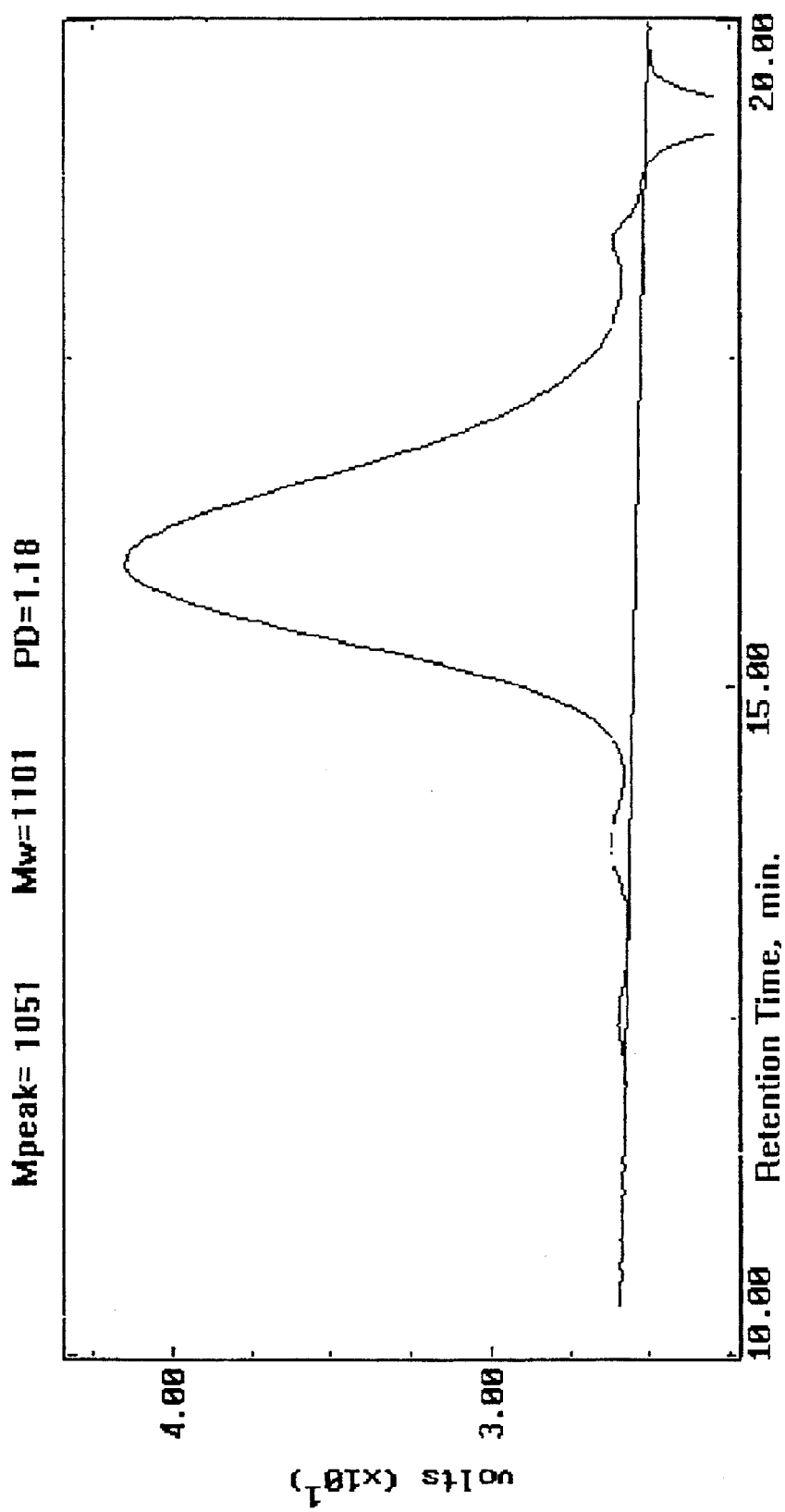
FIG. 2 is a gel permeation chromatogram of the low molecular weight impurity from a supercritical fluid extraction at a $CO_2$ pressure of 2200 psi of CRL8131.
Figure 3:
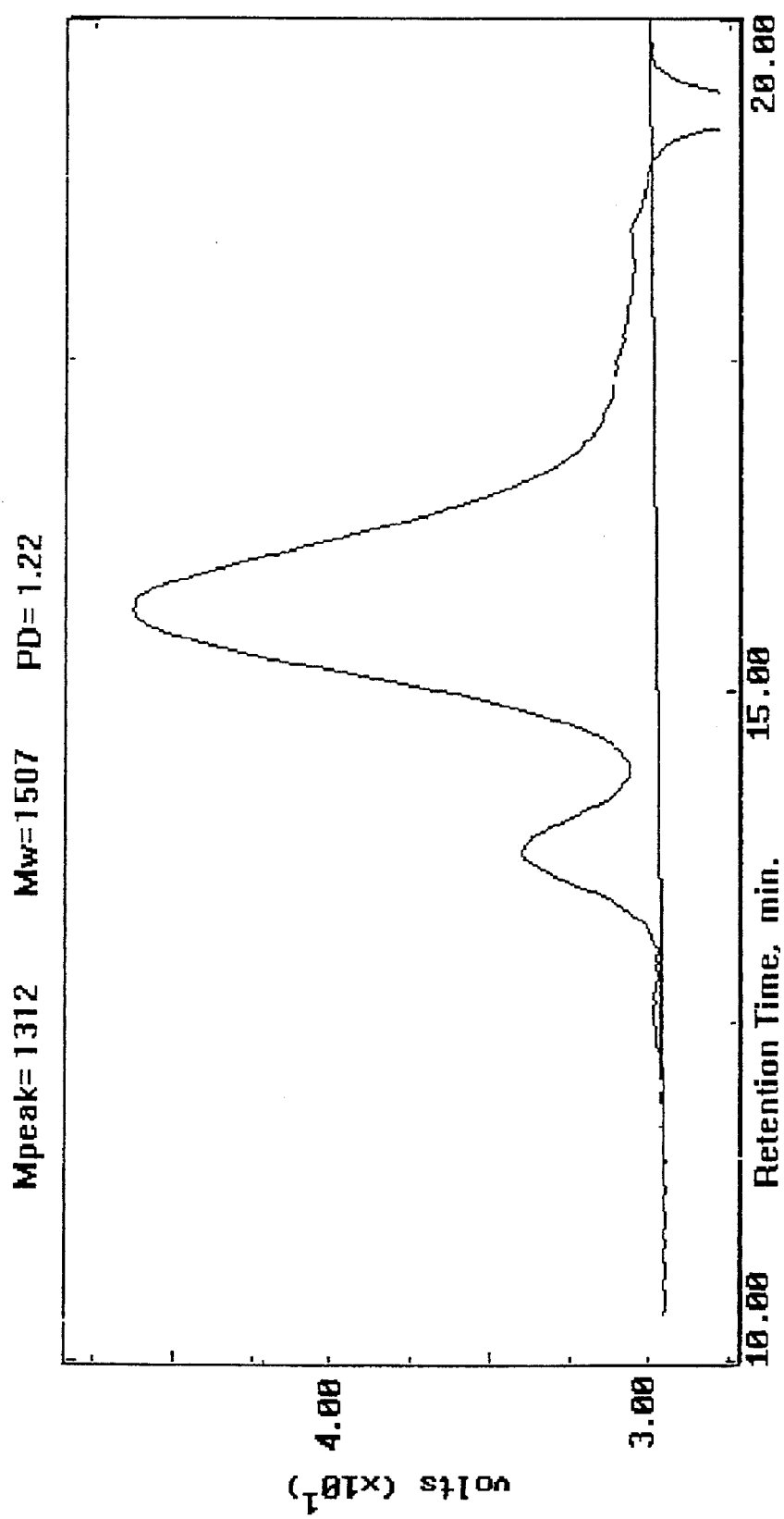
FIG. 3 is a gel permeation chromatogram of the low molecular weight impurity from a supercritical fluid extraction at a $CO_2$ pressure of 3300 psi of CRL8131.
Figure 4:
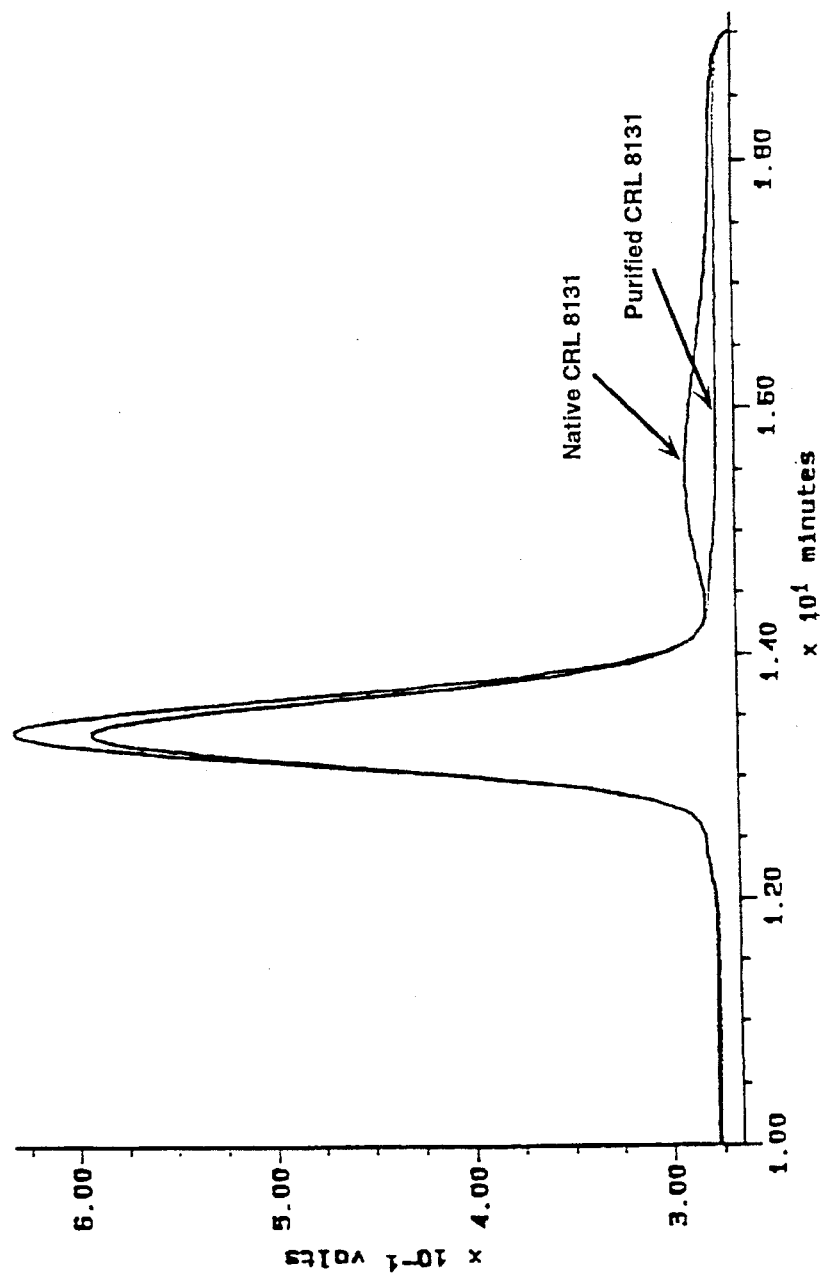
FIG. 4 are gel permeation chromatograms comparing the native CRL8131 and a purified CRL8131 obtained by supercritical fluid extraction of native CRL8131.

From GPC analyses, it is shown that most of the low molecular weight impurity was removed by the supercritical $CO_2$ at 2200 psi. At this pressure range, the extracted material primarily had a single broad peak (FIG. 2) with the peak average molecular weight ranging from 800 to 1000 Daltons. Supercritical $CO_2$ (at 3400 psi) extracted mostly low molecular weight (FIG. 3) but with a small fraction of high molecular weight component. Higher pressure (4400 psi) supercritical $CO_2$ extracted relatively higher molecular weight fractions. The important observation is that the material remaining in the extractor after fractionation (fraction 159-21-19) did not have any low molecular weight components in GPC. It has a single, narrow peak (FIG. 4) with peak average molecular weight of 4091 and polydispersity of 1.04 vs. 1.24 for the starting material.

The fraction 159-21-18 had the accumulation of liquid $CO_2$ soluble fraction of the starting material collected through out the extraction. This fraction had the largest polydispersity of 2.54 with several small peaks in the very low molecular weight region. This fraction also had the highest amount of ethylene glycol (2686 ppm) and propylene glycol (351 ppm). This observation indicates that the starting material can be purified from very low molecular weight components such as ethylene glycol and propylene glycol just by washing with liquid $CO_2$.

EXAMPLE V

The percentage of ethylene oxide as measured from NMR spectra of certain fractions, were higher for supercritical $CO_2$ extractable fractions. The low molecular weight component of CRL8131 has relatively higher ethylene oxide content than the high molecular weight component. It is believed that the fractionation was driven by higher ethylene oxide content in combination with the lower molecular weight. Consequently, the high molecular weight component remaining in the extractor had slightly lower ethylene oxide than the starting material.

The supercritical $CO_2$ extractable, low molecular weight component has relatively higher amount of unsaturation than the high molecular weight component. The unsaturation is probably the result of the side reactions during the polymerization of propylene oxide. These side reactions caused the formation of low molecular weight, unsaturated component. The high molecular weight component has the least amount of unsaturation. On per mole basis, in supercritical $CO_2$ extractable low molecular weight impurities, approximately 60 to 85 percent of the molecules are unsaturated on one end of the chain. This indicates that approximately 60 to 85 percent of the molecules have AB (di) block structure where the high molecular weight fraction has mostly ABA (tri) block structure.

The fractions were also analyzed by FT-IR. We observed that $CO_2$ extractable, low molecular weight impurities have small absorption peaks around 1650 characteristic of unsaturation; whereas, the high molecular weight fraction that remained in the extractor did not have such peaks.

EXAMPLE VI

Figure 7:
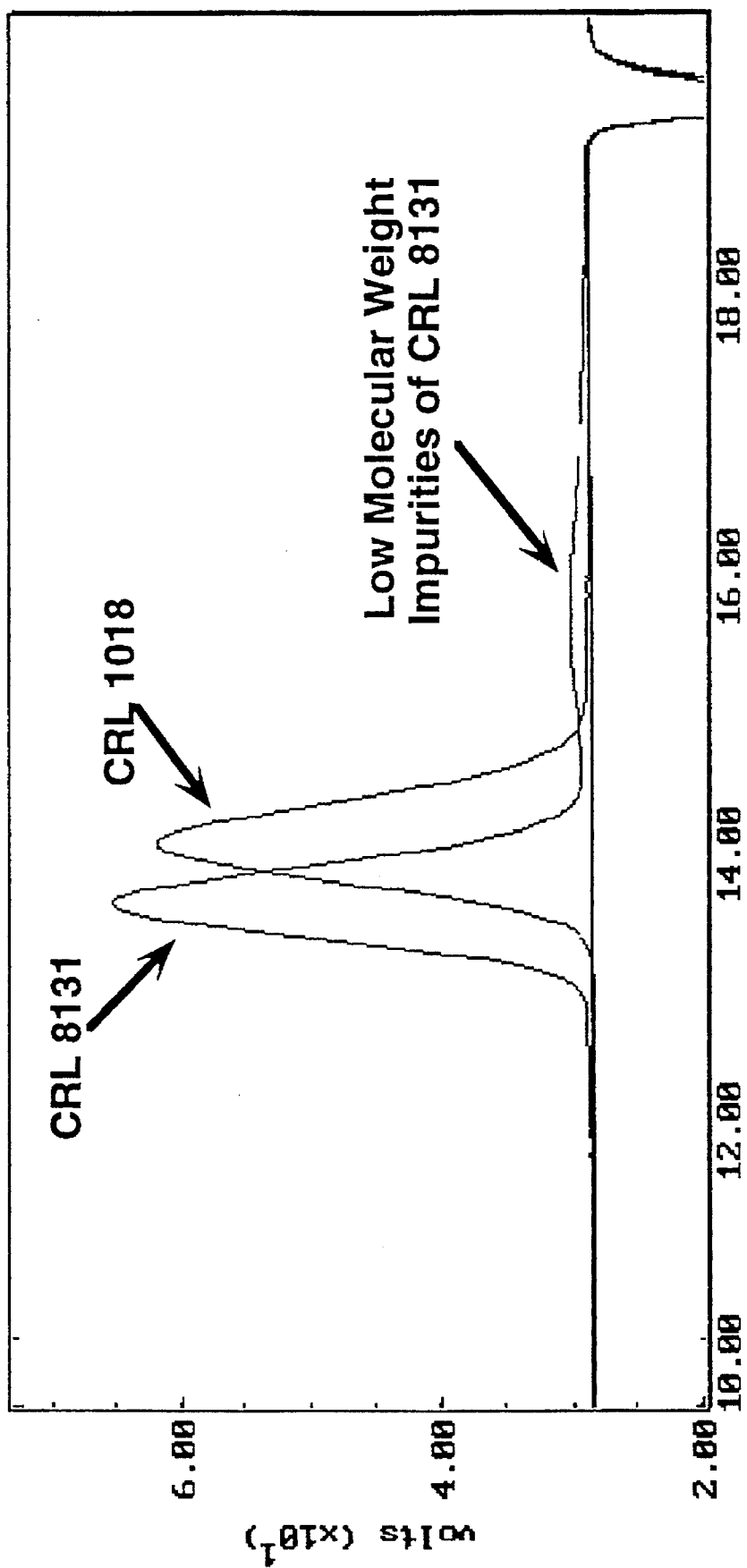
FIG. 7 is the gel permeation chromatograms of a synthetically prepared poloxamer that has significantly low amounts of unsaturation and low molecular weight impurities with low polydispersity compared with a similar commercially available poloxamer CRL8131.

Synthetic preparation of low polydisperse poloxamer CRL1018:

CRL1018 is similar to purified high molecular weight fraction of CRL8131 with regard to lack of low molecular weight impurities and polydispersity. The peak molecular wieght of 1018 is slighly lower than the purified high molecular weight fraction of CRL8131. The CRL1018 is considered part of the present invention. About 0.058 g of Cesium hydroxide monohydrate which was used as a catalyst was mixed with 0.152 g of propylene glycol (initiator) in a reactor. About 7.625 g of propylene oxide was added slowly while heating the reactor at 100° C. Then the polymerization was continued with the addition of about 1.36 g of ethylene oxide at 100° C. After the reaction, the catalyst was removed by heating the reaction product with magnesium silicate and filtered. The weight of the final product is 6.8 grams. The GPC analysis of this polymer showed a single peak with the peak molecular weight of 3675 daltons, weight average molecular weight of 3584 daltons, and polydispersity of 1.043. The peak comprised molecules ranging from 2000 to 6000 daltons. A gel permeation chromatogram of the CRL1018 is shown in FIG. 7

EXAMPLE VII

Additional supercritical fractionation experiments were performed on CRL8131, similar to the method described Example IV. The physical characteristics of the fractions collected during these additional fractionation experiments are described in Table IV.

TABLE IV

| Additional supercritical extraction experiments: | | | | |
|---|---|---|---|---|
| Fraction ID | Peak Mwt | Wt Avg. Mwt. | Polydispersity | Comments |
| Sample: CRL8131 Lot # 120-1; | | | | |
| CRL8131 | 4225 | 3978 | 1.22 | Starting Material |
| 8131-2-1 | 1144 | 1843 | 1.73 | Low Mol. Wt. impurity |
| 8131-2-2 | 3705 | 2469 | 1.54 | Mixture of high and low mol. wt. fractions |
| 8131-2-3 | 3561 | 2558 | 1.40 | Mixture of high and low mol. wt. fractions |
| 9131-2-4 | 3632 | 3269 | 1.49 | Mixture of high and low mol. wt. fractions |
| 8131-2-5 | 3742 | 3711 | 1.09 | High Mol. Wt. fraction |
| 8131-2-6 | 3818 | 3999 | 1.05 | High Mol. Wt. fraction |
| 8131-2-7 | 4015 | 4130 | 1.06 | High Mol. Wt. fraction |
| 8131-2-8 | 4225 | 4221 | 1.07 | High Mol. Wt. fraction |
| 9131-2-9 | 4541 | 4537 | 1.08 | High Mol. Wt. fraction |
| 8131-2-10 | 4785 | 5266 | 1.10 | High Mol. Wt. fraction |
| Sample: CRL8131 Lot # 120-3; | | | | |
| CRL8131 | 4270 | 3953 | 1.27 | Starting Material |
| 8131-3-1 | 1050 | 1450 | 1.43 | Low Mol. Wt. fraction |
| 8131-3-2 | 4060 | 3860 | 1.12 | Mixture of high and low mol. wt. fractions |
| 8131-3-3 | 4310 | 4390 | 1.02 | High Mol. Wt. fraction |
| 8131-3-4 | 4540 | 4600 | 1.02 | High Mol. Wt. fraction |
| 8131-3-5 | 4700 | 5060 | 1.03 | High Mol. Wt. fraction |
| Sample: CRL8131 Lot # 120-2; | | | | |
| CRL8131 | 4350 | 4030 | 1.30 | Starting Material |
| 8131-4-1 | 1030 | 1860 | 1.67 | Low Mol. Wt. fraction |
| 8131-4-2 | 3950 | 2970 | 1.40 | Mixture of high and low mol. wt. fractions |
| 8131-4-3 | 4130 | 3740 | 1.16 | Mixture of high and low mol. wt. fractions |
| 8131-4-4 | 4350 | 4330 | 1.06 | High Mol. Wt. fraction |
| 8131-4-5 | 4700 | 5130 | 1.06 | High Mol. Wt. fraction | xxx

As described in Table IV, the first fraction collected during supercritical extraction was primarily low molecular weight component, and the later fractions were high molecular weight components.

Figure 5:
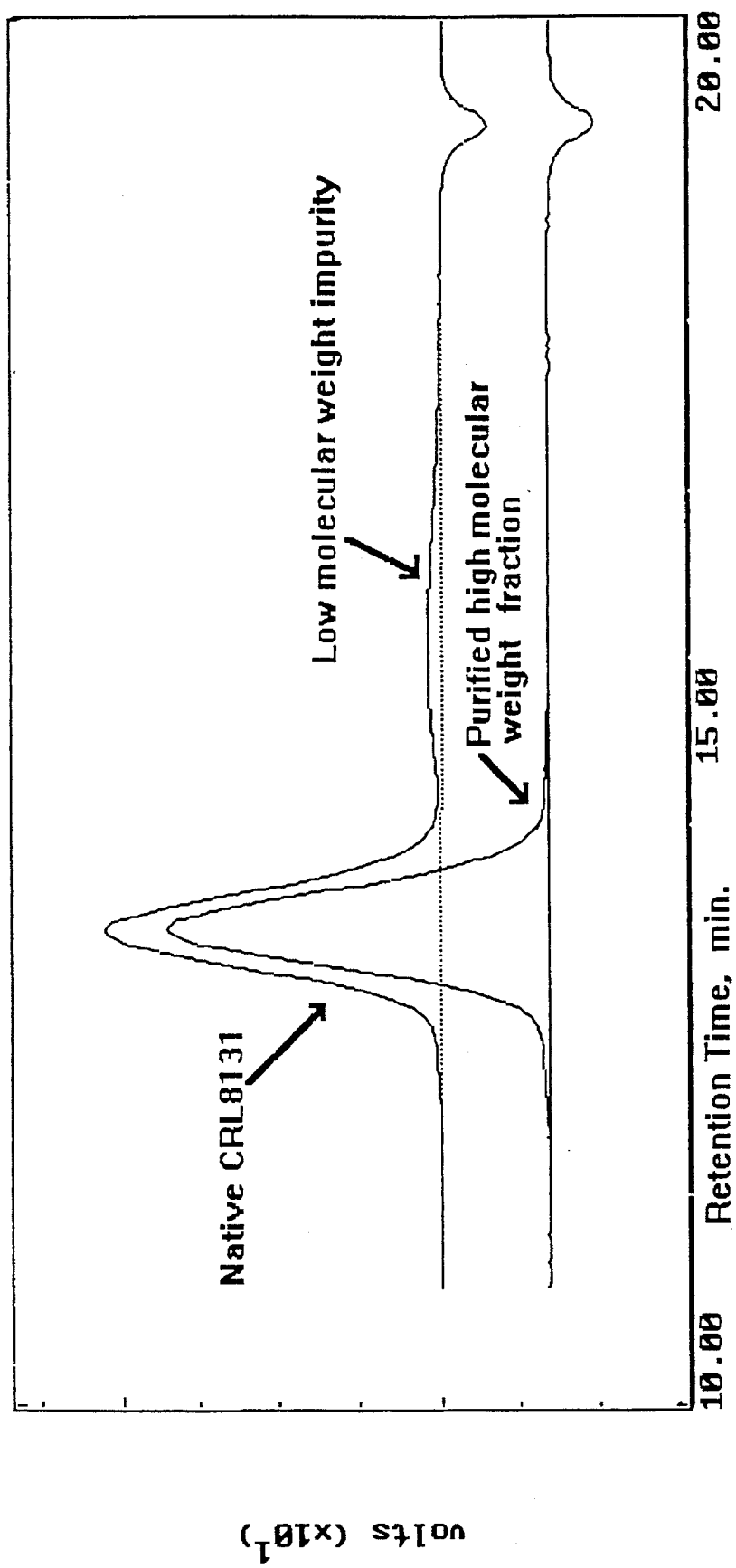
FIG. 5 is a gel permeation chromatogram of the native CRL8131.
Figure 6A:
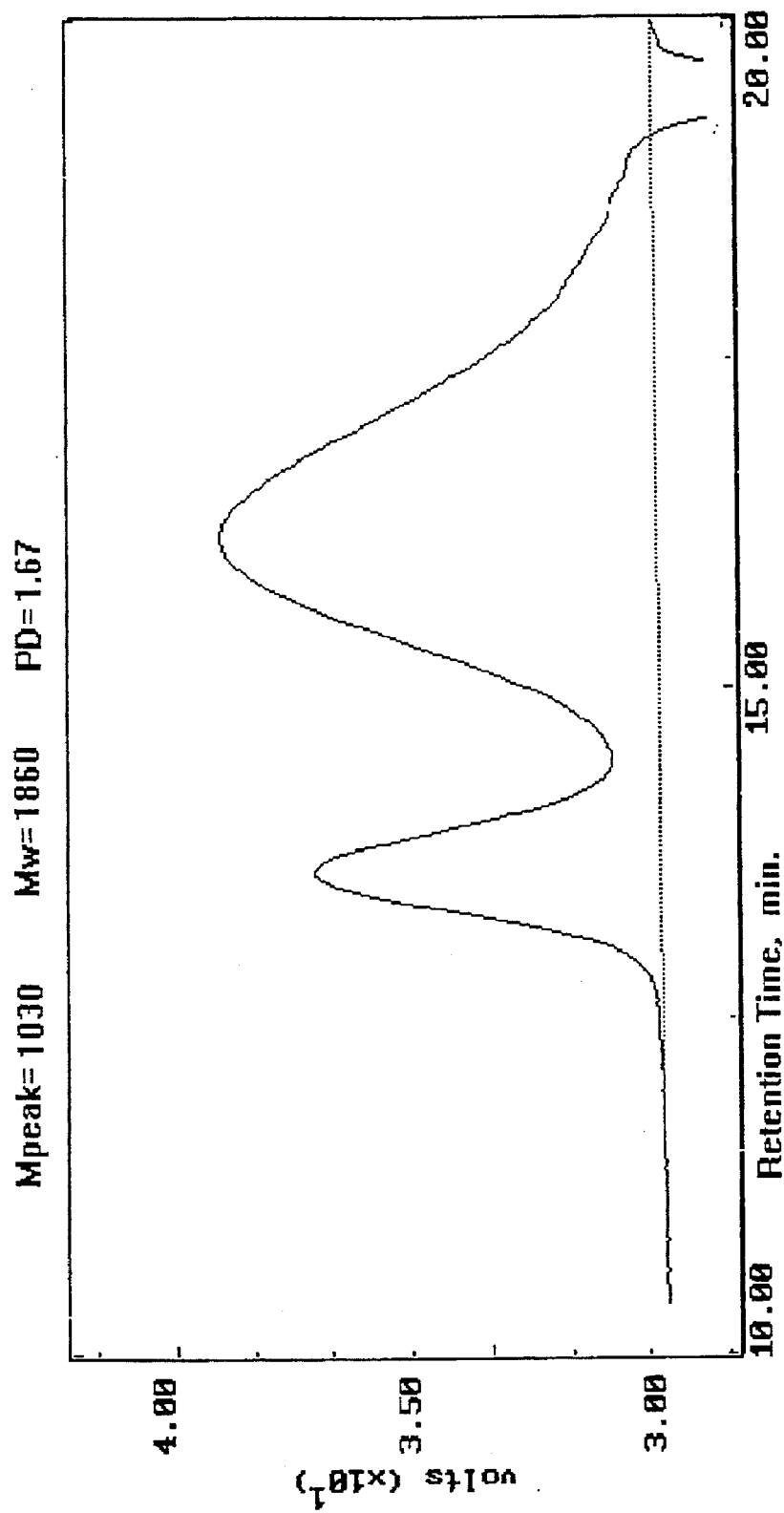
FIG. 6A is a chromatogram of the low molecular weight impurities from super critical fractionation of CRL8131.
Figure 6B:
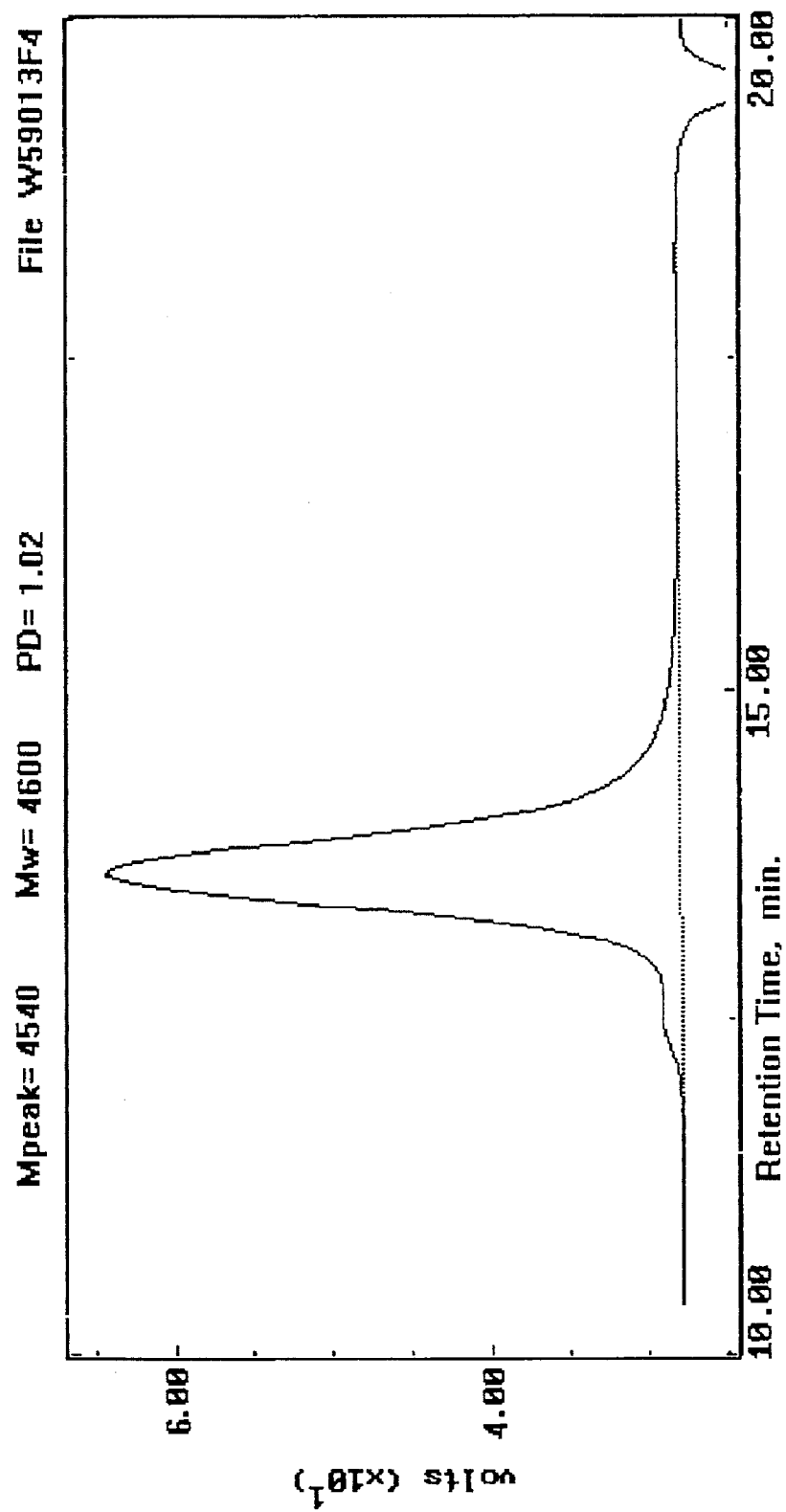
FIG. 6B is the high molecular weight purified fraction from super critical fractionation of CRL8131.

GPC chromatograms for these fractions are shown in FIG. 5 for the native CRL8131, FIG. 6A for a typical low molecular weight impurity and FIG. 6B for a typical purified high molecular weight fraction. This low molecular weight impurity accounted for between 10% and 12% of the total native CRL8131. The low molecular weight impurity in CRL8131 can be defined to contain molecules below 2500 daltons. As shown in FIG. 6A, the low molecular weight fraction obtained by supercritical fluid extraction contained mostly low molecular weight impurities although a small amount of higher molecular weight material was also extracted in this fraction. The typical purified high molecular weight shown in FIG. 6B showed a single peak with a peak molecular weight of approximately 4500, containing molecules ranging from 2500 to 6500 Daltons. The high molecular weight fraction has significantly low polydispersity compared to the native polymer.

EXAMPLE VIII

An experiment comparing the toxicity of low molecular weight impurities, the purified copolymer CRL8131 of the present invention and the native copolymer was conducted as follows:

The test system used was the isovolumetric, Langendorff-perfused rabbit heart. New Zealand White rabbits weighing approximately 3 kg were anesthetized with ketamine (20 mg/kg) and xylazine (4 mg/kg) injected intramuscularly. The blood was heparinized (250 units/kg intravenously) and via a thoracotomy, the heart was excised and placed in cold (4° C.) Krebs-Henseleit solution. After cannulation of the aorta, the heart was immediately flushed with a Krebs solution and suspended within the perfusion system. The time elapsed between the excision of the heart and the beginning of perfusion was 3 minutes.

A modified Langendorff isolated heart system was used in this study. The perfusate was pumped from a reservoir through a blood transfusion filter to the perfusion column. The heart was perfused via the cannulated aorta with a coronary perfusion pressure of (PP) approximately 60 mm Hg. This required a flow (Q) of 25 ml/min. Coronary vascular resistance was estimated as PP/Q. To obtain isovolumetric contractions, a latex balloon filled with fluid (2 to 5 ml) was inserted in the left ventricular cavity via an opening in the left atrium. A fluid filled catheter attached to the monitor was used to measure the left ventricular pressure (LVP). Left ventricular pressure and its electronically obtained first derivative (LV dP/dt) was continuously recorded. Heart rate was monitored via a cardiotachometer triggered by the LVP. The hearts were maintained at 37° C. and were not paced during the perfusion. They were allowed to recover for 35 to 40 minutes before the control measurements. The Krebs Henseleit buffer used for perfusing had the following composition in mM:

| | |
|---|---|
| Na | 155 |
| K | 5.6 |
| Cl | 138 |
| Ca | 2.16 |
| $PO_4$ | 1.19 |
| $HCO_3$ | 2.5 |
| Mg | 0.56 |
| Glucose | 11 |

The buffer was equilibrated with 95% $O_2$ and 5% $CO_2$, and maintained a pH of 7.4 before and during the experiment.

An equilibrium period of 50 minutes was observed to allow LVP, coronary perfusion pressure and heart rate to attain stable levels. Values of the variables were taken at −20 and −10 minutes. At time 0, the poloxamer or vehicle was infused (Harvard infusion pump) into the aortic cannula via a needle in a rubber cuff (2 ml/min). Changes that developed in LVP, heart rate and coronary perfusion were monitored at 5, 10, 15, 20, 30, 45, 60, and 90 minutes.

EXAMPLE IX

Figure 8:
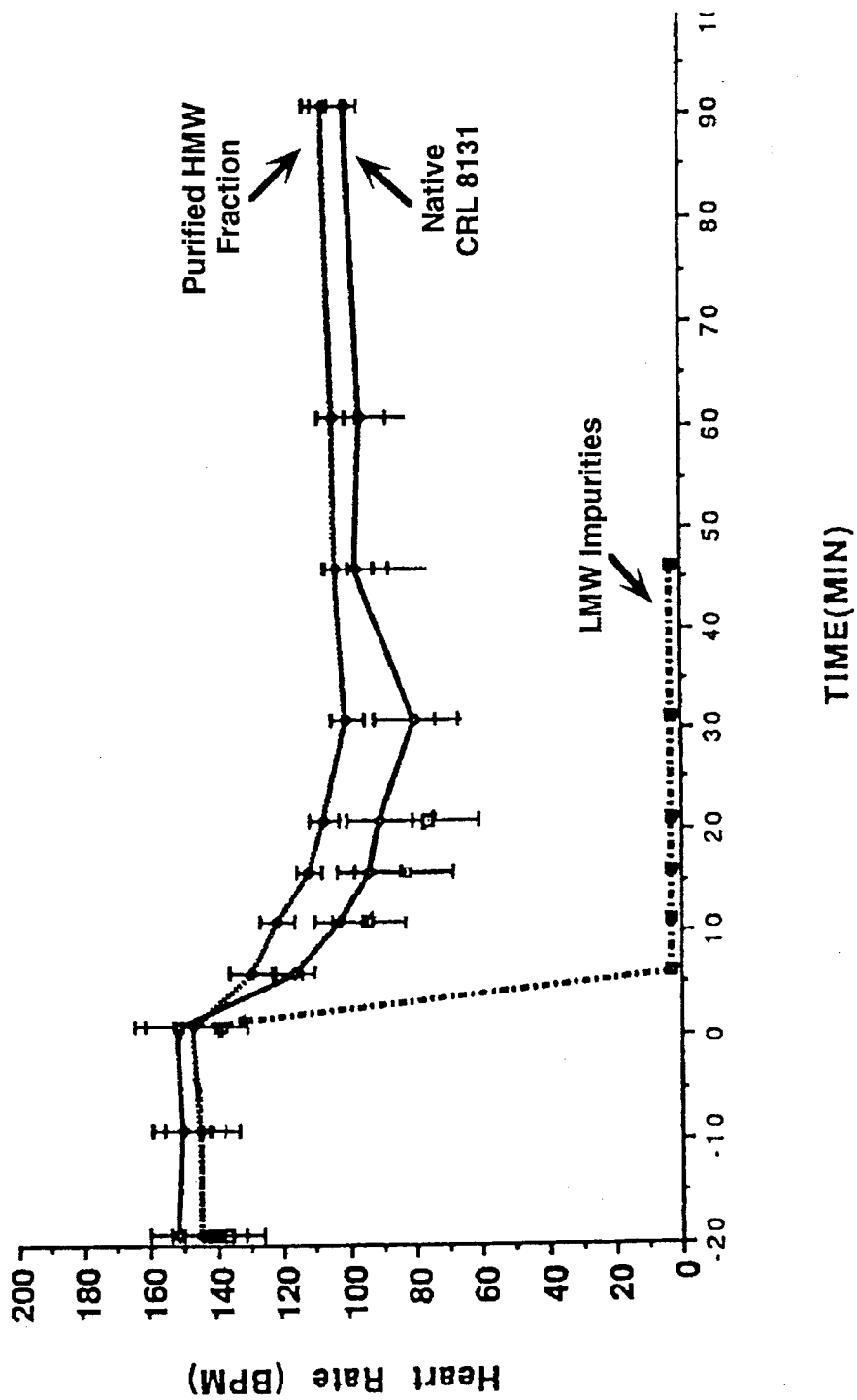
FIG. 8 compares mean heart rate in rabbits that have been treated with a native CRL8131, a fraction containing the low molecular weight impuries of native CRL8131 and purified CRL8131.

As shown in FIG. 8, the mean heart rate for the low molecular weight impurity is depressed to 0 beats per minute (BPM) after infusion of the fraction. Infusion of native CRL8131 showed a marked depression in heart rate. However, the infusion of high molecular weight fraction only showed a modest depression in heart rate.

Figure 9:
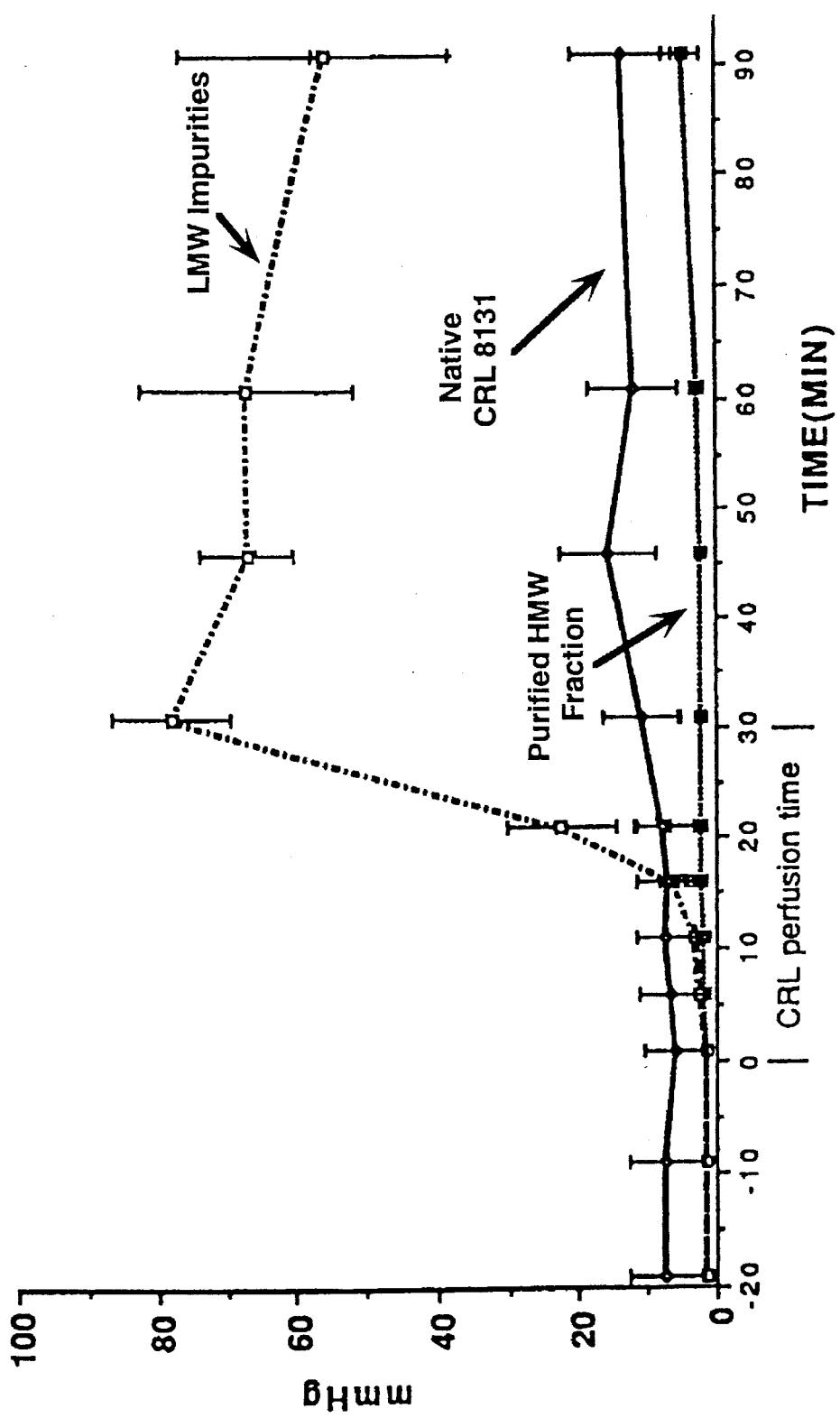
FIG. 9 compares left ventricular diastolic pressure of rabbit hearts that have been treated with a native CRL8131, a fraction containing the low molecular weight impuries of native CRL8131 and purified CRL8131.

The left ventricular diastolic pressure was measured after treatment with the three preparations. The results of these experiments are shown in FIG. 9. The purified high molecular weight fraction had no effect on left ventricular diastolic pressure. However, the low molecular weight impurity drastically increased left ventricular diastolic pressure from just over 0 to nearly 80 mmHg. The native CRL8131 caused a modest increase in left ventricular diastolic pressure.

Figure 10:
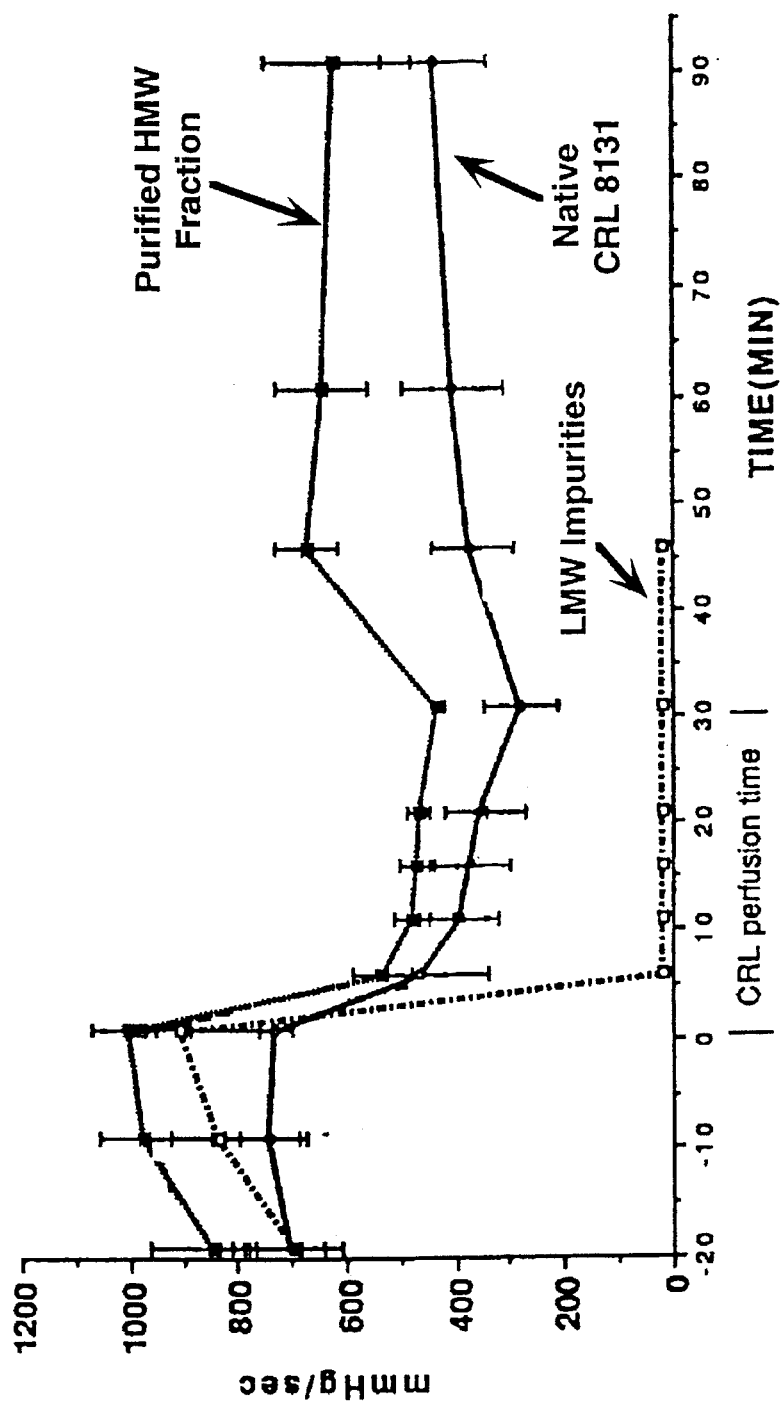
FIG. 10 compares the mean dP/dt of rabbit hearts that have been treated with a native CRL8131, a fraction containing the low molecular weight impuries of native CRL8131 and purified CRL8131.

Next, mean dP/dt was measured in the presence of each of the CRL8131 fractions (FIG. 10). Again, when low molecular weight impurity was administered to the animal, dP/dt initially increased slightly and then fell sharply to 0. The native CRL8131 also caused a decrease in mean dP/dt. The high molecular weight fraction caused a lesser decrease in the dP/dt.

As can be seen from these experiments, the low molecular weight impurity is quite toxic in all of the measurements made. The purified high molecular weight fraction shows the least toxicity when compared to low molecular weight impurity or to native CRL8131.

EXAMPLE X

Effect of CRL8131 fractions on *T. gondii* infection of macrophages

Macrophage monolayers were pretreated with the indicated copolymers for 18 hours. The macrophages were then infected with Toxoplasma gondii at a concentration of approximately two *T. gondii* organisms per macrophage. After one hour, nonphagocytized organisms were removed by washing and the medium plus the copolymer was replenished. Monolayers were fixed and enumerated at 24 hours after challenge. As a positive control, interferon-g, IFN-gamma, (murine recombinant at 200 U/ml) was added to macrophage monolayers 18 hours before challenge with Toxoplasma. These macrophages are activated by the IFN-gamma and readily kill Toxoplasma.

TABLE V

| Fractions | Dose µg/ml | Incubation Time | Percent reduction in # of infected macs | Percent reduction in # Toxo/ infected macs | Percent reduction in # Toxo/100 macs |
|---|---|---|---|---|---|
| Control | 0 | n/a | 0 | 0 | 0 |
| Low Mol. Wt. Impurity | 2 | 0–24 hrs | 15 | 42 | 50 |
| Low Mol. Wt. Impurity | 10 | 2–4 hrs | 39 | 25 | 51 |
| Low Mol. Wt. Impurity | 50 | 2–4 hrs | 76 | 78 | 94 |
| High mol. wt. fraction (purified) | 2 | 0–24 hrs | 63 | 84 | 94 |
| High mol. wt. fraction (purified) | 10 | 2–4 hrs | 69 | 71 | 90 |
| High mol. wt. fraction (purified) | 50 | 2–4 hrs | 83 | 75 | 95 |

As shown in Table IV, high molecular weight fractions of CRL-8131 are most active against Toxoplasma. These fractions demonstrated organism reductions of greater than 90% after incubation with infected macrophages at 10 and 50 µgml for 2 to four hours. These high molecular weight fractions also demonstrated organism reductions of greater than 84% after incubation with infected macrophages at 2 µg/ml for 0 to 24 hours as opposed to only 42% for the low molecular weight fractions.

EXAMPLE XI

Experiments were conducted to examine the in vivo activity against *Toxoplasma gondii* of the purified high molecular weight fraction and the low molecular weight impurity of CRL8131. Both fractions were formulated at 3% drug substance in a vehicle of two percent Tween 80 and 1 percent ethanol and appropriately diluted prior to administrated. A series of experiments were conducted with mice infected by intraperitoneal (IP) injection of tachyzoites of the R.H. strain of *T. gondii*.

Mice were Swiss-Webster females weighing 20 grams at the beginning of the experiment. Infection was IP with $10^3$ tachyzoites. Treatment with the fractions of CRL8131 was administered intraperitoneally. Treatment with the fractions of CRL8131 were administered interperitoneally at doses of 25 mg/kg/day. Treatment was initiated 24 hours after infection and continued every day for 10 days. Mice dying during treatment and after its discontinuation were examined for presence of *T. gondii* tachyzoites in intraperitoneal fluid.

Figure 11:
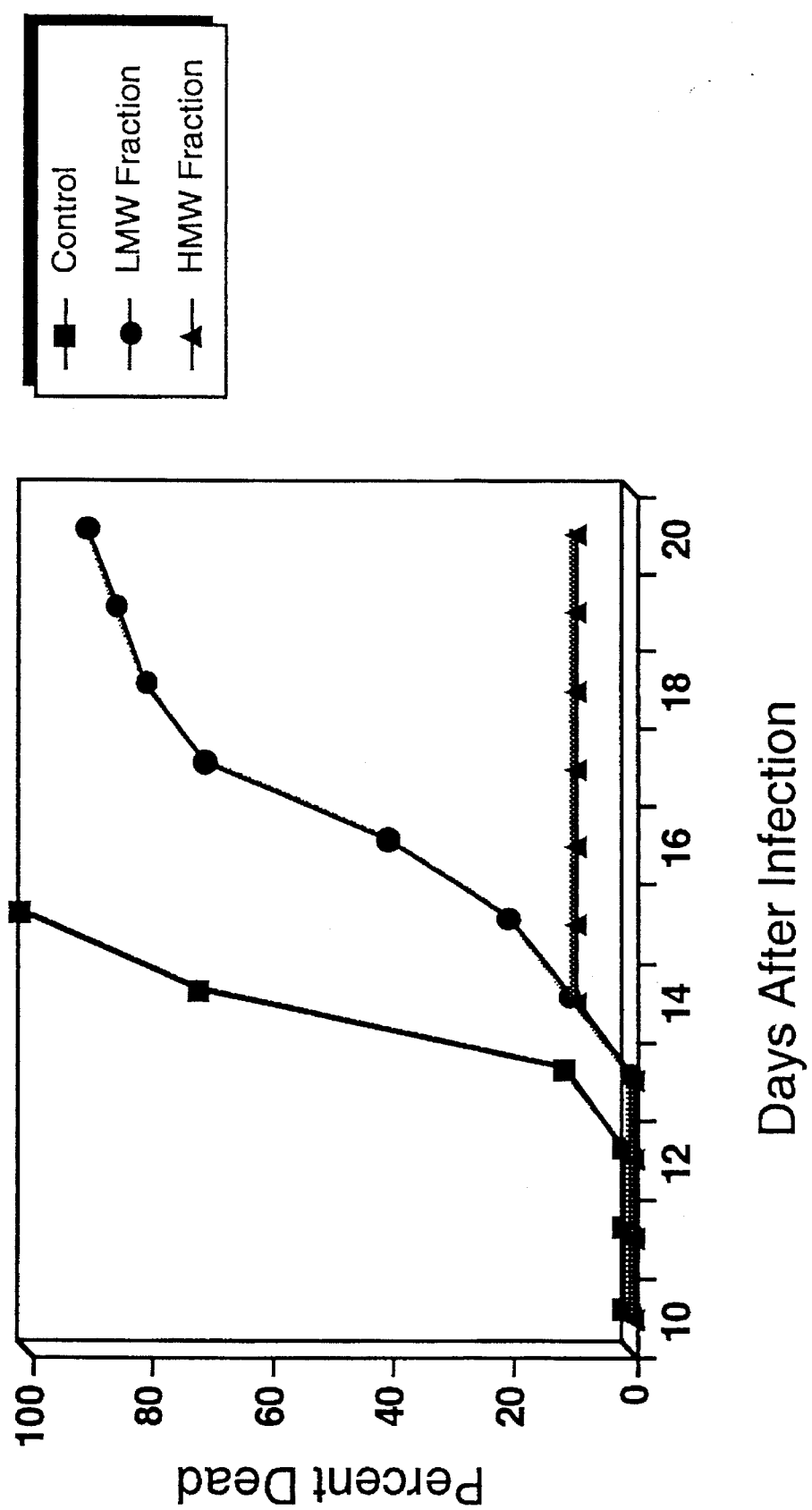
FIG. 11 compares survival of mice infected intraperitoneally with *Toxoplasma gondii* and treated with either purified CRL8131 or the low molecular weight impurities of native CRL8131.

Purified high molecular weight fraction of CRL8131, delivered IP, was clearly superior to the low molecular weight impurities of CRL8131 delivered IP in preventing death. (See FIG. 11) Although not shown, pretreatment of mice in this experiment did not significantly reduce mortality.

It should be understood that the foregoing relates only to a preferred embodiment of the present invention and that numerous modifications or alterations may be made therein without departing from the spirit and the scope of the invention as set forth in the appended claims.

We claim:

1. A polyoxypropylene/polyoxyethylene block copolymer comprising the formula:

$$HO(C_2H_4O)_b(C_3H_6O)_a(C_2H_4O)_bH$$

wherein "a" is an integer such that the molecular weight of the hydrophobe ($C_3H_6O$) is between approximately 1,200 to 15,000 Daltons and "b" is an integer such that the percentage of the hydrophile ($C_2H_4O$) is between approximately 1% and 50% by weight of the total molecular weight of the copolymer and such that the polydispersity value of the copolymer is less than approximately 1.17.

2. The copolymer of claim 1, wherein the polydispersity value is less than approximately 1.10.

3. The copolymer of claim 2 wherein the polydispersity value is less than approximately 1.05.

4. The copolymer of claim 1, wherein the copolymer is substantially free of unsaturation.

5. A polyoxypropylene/polyoxyethylene block copolymer comprising the formula:

$$HO(C_2H_4O)_b(C_3H_6O)_a(C_2H_4O)_bH$$

wherein "a" is an integer such that the molecular weight of the hydrophobe ($C_3H_6O$) is between approximately 2250 to 4000 Daltons and "b" is an integer such that the percentage of the hydrophile ($C_2H_4O$) is between approximately 10% and 40% by weight of the total molecular weight of the copolymer and the polydispersity value of the copolymer is less than approximately 1.17.

6. The copolymer of claim 5, wherein the polydispersity value is less than approximately 1.10.

7. The copolymer of claim 5, wherein the polydispersity value is less than approximately 1.05.

8. The copolymer of claim 5, wherein the copolymer is substantially free of unsaturation.

9. The copolymer of claim 5, wherein "a" is an integer such that the molecular weight of the hydrophobe ($C_3H_6O$) is approximately 3250 Daltons and "b" is an integer such that the percentage of the hydrophile ($C_2H_4O$) is approximately 10% by weight of the total molecular weight of the copolymer and the polydispersity value of the copolymer is less than approximately 1.17.

10. The copolymer of claim 9, wherein the polydispersity value is less than approximately 1.10.

11. The copolymer of claim 9, wherein the polydispersity value is less than approximately 1.05.

12. The copolymer of claim 9, wherein the copolymer is substantially free of unsaturation.

* * * * *